(12) United States Patent
DeBuc

(10) Patent No.: US 11,963,786 B2
(45) Date of Patent: Apr. 23, 2024

(54) SYSTEMS AND METHOD FOR DETECTING COGNITIVE IMPAIRMENT

(71) Applicant: UNIVERSITY OF MIAMI, Miami, FL (US)

(72) Inventor: Delia DeBuc, Miami, FL (US)

(73) Assignee: University of Miami, Miami, FL (US)

( * ) Notice: Subject to any disclaimer, the term of this patent is extended or adjusted under 35 U.S.C. 154(b) by 521 days.

(21) Appl. No.: 17/298,925

(22) PCT Filed: Dec. 6, 2019

(86) PCT No.: PCT/US2019/064889
§ 371 (c)(1),
(2) Date: Jun. 1, 2021

(87) PCT Pub. No.: WO2020/118160
PCT Pub. Date: Jun. 11, 2020

(65) Prior Publication Data
US 2022/0079506 A1 Mar. 17, 2022

Related U.S. Application Data

(60) Provisional application No. 62/900,871, filed on Sep. 16, 2019, provisional application No. 62/776,693, filed on Dec. 7, 2018.

(51) Int. Cl.
*A61B 5/00* (2006.01)
*A61B 3/12* (2006.01)
*A61B 5/398* (2021.01)

(52) U.S. Cl.
CPC ............. *A61B 5/4088* (2013.01); *A61B 3/12* (2013.01); *A61B 5/398* (2021.01); *A61B 5/4842* (2013.01); *A61B 5/489* (2013.01)

(58) Field of Classification Search
CPC ......... A61B 5/4088; A61B 3/12; A61B 5/398; A61B 5/4842; A61B 5/489; A61B 5/004;
(Continued)

(56) References Cited

U.S. PATENT DOCUMENTS

| 2012/0150029 A1* | 6/2012 | Debuc | G06T 7/12 |
| | | | 600/425 |
| 2018/0235467 A1 | 8/2018 | Celenk et al. | |
| 2022/0260591 A1* | 8/2022 | Koronyo | A61B 5/0071 |

OTHER PUBLICATIONS

Supplementary European Search Report dated Jul. 7, 2022 in European Patent Application No. 19893630.
(Continued)

*Primary Examiner* — James C. Jones
(74) *Attorney, Agent, or Firm* — Procopio, Cory, Hargreaves & Savitch LLP

(57) ABSTRACT

Systems, methods, and computer readable media for determining cognitive impairment (CI) in patients are provided herein. Various regional structural-functional parameters of the retina can serve as biomarkers for the detection of CI. The method can include forming a database including a quantification of retinal structure and retinal function of a plurality of eyes associated with a plurality of patients, providing a baseline cognitive impairment (CI) reference. The method can include determining a measure of functionality of neurons in the retina based on an electroretinogram (ERG) of a patient. The method can include determining a structural measure of the first retina based on a generalized dimension spectrum and singularity spectrum of the skeletonized retinal image, and a lacunarity parameter of the skeletonized retinal image. The method can include determining a level of cognitive impairment based on the structural and functional measures.

20 Claims, 7 Drawing Sheets

(58) Field of Classification Search
CPC ............... A61B 5/7267; A61B 3/0025; G06T 2207/20044; G06T 2207/30041; G06T 7/0012; G06T 7/48; G06V 2201/03; G06V 40/14; G06V 40/18
See application file for complete search history.

(56) References Cited

OTHER PUBLICATIONS

Hilal Saima et al., "Microvascular network alterations in retina of subjects with cerebral small vessel disease", Neuroscience Letters, vol. 577, Aug. 8, 2014, pp. 95-100, XP029039146.
T.J. MacGillivray et al., "Retinal imaging as a source of biomarkers for diagnosis, characterization and prognosis of chronic illness or long-term conditgions", British Journal of Radioligy, vol. 87, No. 1040, Aug. 1, 2014, p. 20130832, XP055462052.
Popovic Natasa et al., "Fractal dimension and lacunarity analysis of retinal microvascular morphology in hypertension and diabetes", Microvascular Research, Academic Press, US, vol. 118, Feb. 22, 2018, pp. 36-43, XP085393828.
International Search Report and Written Opinion for corresponding patent application No. PCT/US2019/064889, dated Feb. 25, 2020, in 10 pages.

\* cited by examiner

SYSTEMS AND METHOD FOR DETECTING COGNITIVE IMPAIRMENT

BACKGROUND

Technical Field

This disclosure relates to the diagnosis of cognitive impairment (CI). More specifically, this disclosure relates to the correlation between the retinal vascular complexity and neurodegenerative changes in patients with CI using a multimodal approach.

Related Art

The development of effective therapies for CI, especially due to Alzheimer's disease, places emphasis on early diagnosis (e.g., during the condition during the prodromal phase). Alzheimer's Disease (AD) and other related dementia diseases are diagnosed through expensive and invasive methods, such as PET and cerebrospinal fluid assessment via a spinal tap. Therefore, there is a desire for a comparatively lower cost and noninvasive method that may aid in the early diagnosis of the disease.

SUMMARY

CI is not limited to the brain but also affects the retina. The human retina is an extension of the brain characterized by similarities in vascular and neural structures. In addition, retinal imaging can be attained noninvasively at low cost; the human retina offers a noninvasive window to identify retinal vascular and neural biomarkers of brain diseases.

The complications of CI are not only limited to the brain but also affect the retina for which the loss of retinal ganglion cells has been associated with neurodegeneration in the brain. The loss of retinal ganglion cells in individuals with CI may be related to reduced vascular demand and a potential remodeling of the retinal vascular branching complexity. Retinal imaging biomarkers can provide a low cost and noninvasive alternative for the diagnosis of CI. The retinal vascular branching complexity of patients with CI can be characterized using the singularity spectrum, multifractal dimension and lacunarity parameter. A reduced vascular branching complexity can be observed in subjects with CI when compared to age- and sex-matched cognitively healthy controls. These controls can be accumulated through testing and diagnostics, with the resulting data stored in a database for later correlation.

Quantification of the retinal structure and function can be conducted for every subject using advanced retinal imaging, full-field electroretinogram (ERG), and visual performance exams. The retinal vascular parameters can be determined or otherwise calculated using the Singapore Institute Vessel Assessment software. The Montreal Cognitive Assessment (MoCA) can be used to measure CI. Pearson product moment correlation can be performed between variables.

In one associated study, of 69 participants (n=69), 32 had CI (46%). Significantly altered microvascular network were found in individuals with CI (larger venular-asymmetry factor: 0.7±0.2) compared with controls (0.6±0.2). The vascular FD was lower in individuals with CI (capacity, information and correlation dimensions: D0, D1 & D2 (mean±SD): 1.57±0.06; 1.56±0.06; 1.55±0.06; age 81±6 ys) versus controls (1.61±0.03; 1.59±0.03; 1.58±0.03; age: 80±7 ys). Also, drusen-like regions in the peripheral retina along with pigment dispersion were noted in subjects with mild CI. Functional loss in color vision as well as smaller ERG amplitudes and larger peak times were observed in the subjects with CI. Pearson product moment correlation showed significant associations between the vascular parameters (artery-vein ratio, total length-diameter ratio, D0, D1, D2 and the implicit time (IT) of the flicker response but these associations were not significant in the partial correlations. Thus, there are multimodal retinal markers that may be sensitive to CI decline, and evidence that there is a statistical trend pointing to the correlation between retinal neuronal dysfunction and microvasculature changes suggesting that retinal geometric vascular and functional parameters are associated with physiological changes in the retina due to CI. Analysis of combined, multimodal structural-functional parameters (as opposed to only individual biomarkers), may provide a useful methodology for diagnosis of CI.

One aspect of the disclosure provides a method for determining cognitive impairment (CI) implemented by at least one processor. The method can include forming a database including a quantification of retinal structure and retinal function of a plurality of eyes associated with a plurality of patients, the quantification providing a baseline cognitive impairment (CI) reference. The method can include receiving an electroretinogram (ERG) of a retina of a patient. The method can include determining a measure of functionality of neurons in the retina based on the ERG. The method can include receiving a retinal image of the retina. The method can include skeletonizing the retinal image as a skeletonized retinal image. The method can include determining a structural measure of the first retina based on a generalized dimension spectrum and singularity spectrum of the skeletonized retinal image, and a lacunarity parameter of the skeletonized retinal image. The method can include comparing the measure of functionality and the structural measure of the retina to the database. The method can include determining a level of cognitive impairment of the patient based on the comparing.

The method can include updating the database with the measure of functionality and the structural measure of the retina. The method can include subdividing the skeletonized retinal image into multiple subregions. The method can include determining a structural measure of the each subregion of the multiple subregions based on a generalized dimension spectrum and singularity spectrum of each subregion. The method can include determining a structural measure of the each subregion of the multiple subregions based on a lacunarity parameter of each subregion. The retinal image can include an image of an entire branching pattern of the retina observable in a 20°-200° field of view. The quantification of the retinal function can include a plurality of ERGs associated with patients known to have a level of CI. The quantification of the retinal structure can include a plurality of generalized dimension spectrum and a singularity spectrum associated with retinal images associated within patients known to have a level of CI.

The database can further include the caliber, asymmetry factor, tortuosity, and network complexity of the retinal microvasculature (arteries and veins) with respect to functional features (e.g., contrast sensitivity, electrical response through ERGs), concomitant with both fractal-vascular and neural analysis. The lacunarity can include a measure of coarseness of the skeletonized retinal image.

Another aspect of the disclosure provides a system for determining cognitive impairment (CI). The system can include a database including a quantification of retinal structure and retinal function of a plurality of eyes associated with a plurality of patients, the quantification providing a baseline cognitive impairment (CI) reference; and The system can include at least one processor. The at least one processor can receive an electroretinogram (ERG) of a retina of a patient. The at least one processor can determine a measure of functionality of neurons in the retina based on the ERG. The at least one processor can receive a retinal image of the retina. The at least one processor can skeletonize the retinal image as a skeletonized retinal image. The at least one processor can determine a structural measure of the first retina based on a generalized dimension spectrum and singularity spectrum of the skeletonized retinal image, and a lacunarity parameter of the skeletonized retinal image. The at least one processor can compare the measure of functionality and the structural measure of the retina to the database. The at least one processor can determine a level of cognitive impairment of the patient based on the comparing.

The at least one processor can update the database with the measure of functionality and the structural measure of the retina. The at least one processor can subdivide the skeletonized retinal image into multiple subregions. The at least one processor can determine a structural measure of the each subregion of the multiple subregions based on a generalized dimension spectrum and singularity spectrum of each subregion, and a lacunarity parameter of each subregion.

Another aspect of the disclosure provides a non-transitory computer-readable medium storing instructions for determining cognitive impairment (CI) in patients. The instructions can cause the one or more processors to form a database including a quantification of retinal structure and retinal function of a plurality of eyes associated with a plurality of patients, the quantification providing a baseline cognitive impairment (CI) reference. The instructions can cause the one or more processors to receive an electroretinogram (ERG) of a retina of a patient. The instructions can cause the one or more processors to determine a measure of functionality of neurons in the retina based on the ERG. The instructions can cause the one or more processors to receiving a retinal image of the retina. The instructions can cause the one or more processors to skeletonize the retinal image as a skeletonized retinal image. The instructions can cause the one or more processors to determine a structural measure of the first retina based on a generalized dimension spectrum and singularity spectrum of the skeletonized retinal image, and a lacunarity parameter of the skeletonized retinal image. The instructions can cause the one or more processors to comparing the measure of functionality and the structural measure of the retina to the database. The instructions can cause the one or more processors to determine a level of cognitive impairment of the patient based on the comparing.

Another aspect of the disclosure provides an apparatus for determining cognitive impairment (CI) having a database including a quantification of retinal structure and retinal function of a plurality of eyes associated with a plurality of patients, the quantification providing a baseline cognitive impairment (CI) reference. The apparatus can have means for receiving an electroretinogram (ERG) of a retina of a patient. The apparatus can have means for determining a measure of functionality of neurons in the retina based on the ERG. The apparatus can have means for receiving a retinal image of the retina. The apparatus can have means for skeletonizing the retinal image as a skeletonized retinal image. The apparatus can have means for determining a structural measure of the first retina based on a generalized dimension spectrum and singularity spectrum of the skeletonized retinal image, and a lacunarity parameter of the skeletonized retinal image. The apparatus can have means for comparing the measure of functionality and the structural measure of the retina to the database. The apparatus can have means for determining a level of cognitive impairment of the patient based on the comparing.

Other features and advantages of the disclosure will be apparent upon review by one of ordinary skill in the art.

BRIEF DESCRIPTION OF THE DRAWINGS

The details of embodiments of the present disclosure, both as to their structure and operation, can be gleaned in part by study of the accompanying drawings, in which like reference numerals refer to like parts, and in which.

DETAILED DESCRIPTION

Figure 1:
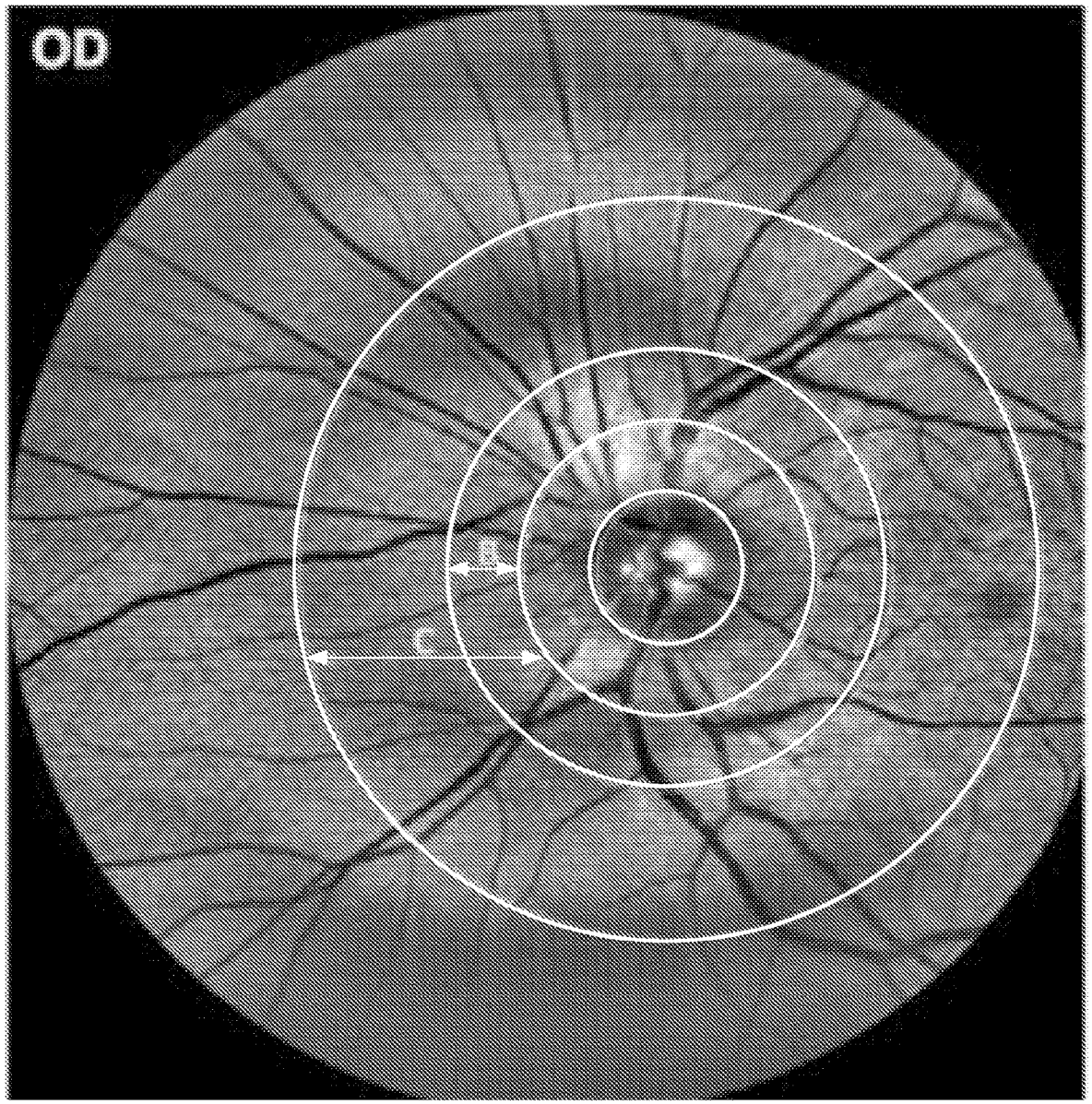
FIG. 1 is an exemplary retinal image.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Whole Retina Branching Pattern

The human retina is an extension of the brain characterized by similarities in vascular and neural structures. The complications of cognitive impairment (CI) are not limited to the brain but also affect the retina for which the loss of retinal ganglion cells has been associated with neurodegeneration in the brain. The loss of retinal ganglion cells in individuals with CI may be related to reduced vascular demand and a potential remodeling of the retinal vascular branching complexity. Retinal imaging biomarkers may provide a low cost and non-invasive alternative for the diagnosis of CI. Cognitive impairment is a substantial source of disability, where attention and concentration, episodic memory, executive function and speed of information processing are the most commonly affected brain functions. A formal cognitive evaluation may require several hours and it is costly. Also, it suffers from several limitations such as not being able to assess the subject's functional status as well as being susceptible to education, cultural, and language influences, which limits their utility as screening tests in general and multi-ethnic populations. The cognitive function is sensitive to many potential disruptive factors such as normal aging as well as disease or injury. Cognition can also be affected temporarily by depression, sleep disturbances, menopause or fatigue, tension and emotional stress. Also, the cognitive function can be affected in many ways when an individual experience a traumatic event, whether physical (e.g., head injury) or psychological (PTSD). Also, different cognitive impairments are reported in car accidents and falls. As used herein, CI refers to mental or cognitive decline. Such cognitive decline can be due to non-traumatic conditions such as dementias or other neurological conditions. In some cases, such cognitive decline can also be due to physical trauma (e.g., head injury).

Provided that vascular and functional patterns of the retina could be highly dissimilar and may have identical FD or be multifractal, an analysis based only on FD calculations is not able to fully characterize objects with fractal properties. Therefore, two additional approaches such as the lacunarity parameter and singularity spectrum analysis can be used to diagnose CI. Overall, the full spectrum of the disclosed methods takes advantage of the multifractal dimension of the retinal microvasculature network, which is a metric that characterizes how optimal and efficient could be the blood distribution in the retina. These assessments can provide better understanding of the morphological and physiological changes that result from disorders such as cognitive decline.

Although vessel density analysis can be used to characterize the retinal microvasculature network, the density is not a scale invariant metric (i.e., variations in vessel diameter can alter density), and thus provides an incomplete analysis for comparison across dissimilar retinal tissue networks (e.g., microvascular network of a healthy retina vs. diabetic retina).

Electroretinogram-Related

The use of the full field ERG can be used to determine whether dysfunction of preganglionic elements may also occur in cognitive deterioration due to AD. Possible dysfunction of preganglionic elements could explain the increase in PERG P50-wave implicit time observed in AD patients and this is supported by data obtained in glaucoma or in multiple sclerosis in which the delay of the P50-wave implicit time could be ascribed to a dysfunction of both ganglionic and preganglionic elements. The PERG-50 wave is a metric obtained with pattern-ERG (PERG) as known in the art. Moreover, flash ERG can be used to demonstrate dysfunction of the retina under photopic and scotopic conditions in patients with dementia with Lewy bodies. Studies related to this disclosure showed that the retinal dysfunction may be related to slight alteration of the photoreceptors and numerous pale inclusions in the outer plexiform layer found at the post-mortem examination, suggesting specific retinopathy. In general, the ERG can be used to objectively measure the function of the retinal neurons and/or their electrical response. The blood circulation in the eye is of decisive importance for the type and the shape of the electroretinogram.

Significantly reduced a-wave amplitude can indicate abnormal photoreceptor function associated to a longer response of the rods under scotopic conditions. The association between the retinal vascular attenuation and the severity of the scotopic full-field alteration can be associated with cone degeneration (e.g., retinitis pigmentosa) for which oxidative stress has been suggested to play a potential pathogenic role like in AD. Moreover, a substantial decrease in mixed rod-cone responses (i.e., decreased a- and b-wave amplitudes) has been noted in mice carrying ApoE-+4 allele of apolipoproteine E4 which is the most prevalent genetic risk factor for the late-onset AD that acts in synergy with Ab. Consequently, the bioelectric activity of the retina with ERG can serve as a valuable biomarker indicating cognitive impairment at the early stage.

Fractal Dimension, Singularity Spectrum and Lacunarity-Related

The branching pattern of the microvascular retinal network can be characterized by fractal and lacunarity analyses. In particular, the complexity of the human retinal microvascular network cannot be precisely quantified using Euclidean geometric parameters because its vascular branching pattern holds a fractal structure characterized by self-similarity and scaling, and it is determined in terms of fractional powers which describe the non-Euclidean shapes. The retinal vasculature network could be quantified with numerous methods of fractal analysis. The multifractal behavior of the retinal vascular network is characterized by the generalized dimension spectrum (Dq versus q) and the singularity spectrum ($f(\alpha)$ versus $\alpha$). The vascular fractal dimension (FD) is an average measure of complexity that describes "global" features of the whole branching pattern of the retinal vascular tree. Therefore, a more complex branching pattern denotes a larger FD value. The FD method can help characterize the retinal microvascular network of patients to help determine cognitive impairment. The multifractal behavior of the retinal microvascular network is characterized by the generalized dimension spectrum (Dq vs. q, where Dq represents the FD at the qth order or exponent) and the singularity spectrum ($f(\alpha)$ vs. $\alpha$ which represents the whole spectrum of fractal dimensions. Hence, q represents values from $-10$ to $+10$ with an increment of 1. These values are computed and then averaged with their standard deviations at each value of q. The Dq (e.g., $D_0$, $D_1$, and $D_2$) describes the multifractal characteristics of an object when condition $D_0 \geq D_1 \geq D_2$ is satisfied, being $D_0$, $D_1$, and $D_2$ the capacity dimension, information or entropy dimension, and correlation dimension, respectively. The singularity spectrum for multifractal object is typically a parabola with concavity facing down characterized by the height ($\Delta f$), width ($\Delta \alpha$), and asymmetry (A). The more the $\Delta \alpha$, the stronger the multifractality is, and the more complex the pixel distribution within the image is. Also, greater values of the singularity exponents ($\alpha_0, \alpha_1, \alpha_2$) of the singularity spectrum $f(\alpha)$ at $q=0, 1, 2$ indicate greater singularities or maxima.

On the other hand, lacunarity ($\Lambda$) is a parameter commonly used to describe texture or coarseness of an image, and can also differentiate two objects with similar FD. Considering that the $\Lambda$ parameter measures the heterogeneity or gap dispersion within an object, a high $\Lambda$ describes an object with large gaps; while a low $\Lambda$ is associated to homogeneous objects characterized by gaps that are all the same.

Regional Branching Pattern

The foregoing systems and methods consider the whole retinal branching pattern to investigate the correlation between retinal vascular complexity and neurodegenerative changes in patients with cognitive impairment. There are also combined structural-functional metrics, instead of individual biomarkers that may be sensitive to the decline of cognitive impairment. Specifically, a statistical trend indicates correlation between retinal neuronal dysfunction and microvasculature changes suggesting that retinal geometric vascular and functional parameters might be associated with physiological changes in the retina due to cognitive impairment. However, the studies associated with the disclosure suggested the need to conduct a regional analysis instead of considering the whole retinal branching pattern. Including analyses of regional portions of the retina, as opposed to the "whole" retina branching pattern alone, can provide associations between vascular and functional parameters while controlling for the other covariates.

Studies associated with the regional branching pattern first investigated whether fractal complexity and lacunarity analyses performed in sectoral regions of the retina may reveal alterations in patients with cognitive impairment that may be masked in the analysis when considering the whole retinal branching pattern. Second, they investigated how the microvascular network complexity and neural function alterations in these sectoral regions of the retina contribute to differences in cognitive function. In general, multivariate retinal biomarkers in the sectoral regions reflect distinctive eye-brain signatures of cognitive impairment that can have significant "unique" associations with the onset and progression of cognitive decline.

Multifractal analysis along with lacunarity and multifractal spectra analyses in sectoral regions of the retina can provide a convenient and robust methodology for measuring significant changes in both neural function and retinal vessel morphology (e.g., structure) associated with CI decline, and can add additional diagnostic value to the use of retinal biomarkers for early diagnosis of CI. The use of a multimodal diagnostic biomarker approach based on the retinal structure-function relationship can have the advantage of a low-cost implementation in community settings. Analysis of combined structural-functional parameters in sectoral regions of the retina, instead of individual biomarkers, may provide a useful clinical marker of cognitive impairment.

SUMMARY OF METHODS

Whole Branching Pattern

Multimodal parameters characterizing the structure and function of the retina can be compared to evaluate the retinal vascular alterations regarding the retinal function in patients with cognitive impairment. A first method can be used to obtain multiple retinal measures, such as structural (FD and lacunarity) (see FIG. 1 and FIG. 2) and functional (ERG) indicators of the retina. This specific methodology provides link between, for example, the caliber, tortuosity, and network complexity of the retinal microvasculature (arteries and veins) with respect to functional features (e.g., contrast sensitivity, electrical response through ERGs), concomitant with both fractal-vascular and neural analysis.

The bioelectrical (e.g., functional) activity of the retinal neurons can be measured with a full-field electroretinogram (ERG, RETeval™, LKC Technologies, Inc., Gaithersburg, MD, United States) according to the International Society for Clinical Electrophysiology of Vision (ISCEV) protocol. ERG amplitudes and implicit time values can be measured consistent with the recommendations by the ISCEV. The protocol used was the ISCEV 6 step, light-adapted first. Assessments can include light-adapted ERG (stimulus strength, 3.0 cd·s/m$^2$; frequency, 28.3 Hz flicker response). Implicit times and amplitude values of the ERGs elicited by 141 to 424 flashes can be processed separately for each eye.

The involvement of the visual cortex may be the cause for dysfunction of the elementary visual sensation that may be involved in the development of visual cognitive deficits and vision-related behavioral symptoms. Moreover, flash ERG can be used to demonstrate dysfunction of the retina under photopic and scotopic conditions in patients with dementia with Lewy bodies. The use of the full-field ERG can also help determine whether dysfunction of preganglionic elements may also occur in AD. The RETeval™ system is a full-field flicker ERG recording device designed as a low-cost handheld alternative to traditional ERG screening without the need for mydriasis. It can perform measurements in both eyes in about 3 minutes without any eye contact. Also, various flicker-based or single-flash based protocols are available through a protocol chooser that enables other ERG/VEP tests. The intensity of the flash source of this device is calibrated consistently with the light-adapted 3.0 flicker ERG protocol of the ISCEV standard. The ERG examination was performed by an experienced examiner trained in the use of the RETeval™ unit.

For baseline empirical reference, cognitive function can be assessed using a cognition test, such as the Montreal Cognitive Assessment (MoCA), a widely-used screening test for detecting cognitive impairment. The MoCA can be used to assess the short-term memory, visuospatial abilities, executive functions, language abilities, orientation to time and place as well as attention, concentration, and working memory in all study participants. Beyond the use of study participants, the baseline classifications can be used to stratify patients, providing an initial reference to adjudge CI in patients. The MoCA is used as a primary example of a cognitive assessment herein, but other methods are also applicable to establish a baseline reference. For example, the Mini-Mental State Exam (MMSE), and Mini-Cog cognitive tests, as well as certain other physiological diagnostic tests (e.g., Magnetic Resonance Imaging (MRI), positron emission tomography (PET), computerized tomography (CT), etc.) are also possible for use in establishing a baseline cognitive assessment database.

The MoCA focuses on several cognitive domains: short-term memory, visuospatial abilities, executive functions, language abilities, orientation to time and place as well as attention, concentration, and working memory. The MoCA total score range is from 0-30, with lower scores (<26 points) indicating poorer cognitive ability. Patients with a score of ≥26 points are generally considered as having normal cognition with an average score of 27.4, compared with 22.1 in people with mild cognitive impairment (MCI) and 16.2 in people with AD. One of the advantages of the MoCA test is that it measures an essential component of dementia (i.e., executive function) that is not measured by the mini-mental state examination (MMSE). It also allows cognitive testing for those who are visually impaired. As the loss in cone function could be caused by ocular disorders, neurological diseases, systemic disorders, and trauma to the eye or brain, all study subjects were tested for acquired color vision deficiencies. Therefore, the type and severity of color vision deficiency was tested from the right eye to the left eye in a dark room using a commercially available, tablet-based Cone Contrast Test unit (CCT, Provideo CCT Plus System, Innova Systems Inc., Burr Ridge, IL, United States). The CCT scores, expressed in the range from 0 to 100, can be indicated of ocular disorders.

FIG. 1 is an exemplary retinal image. The example image was obtained with the EasyScan unit (i-Optics Corporation, The Netherlands) and analyzed with the Singapore I Vessel Assessment (SIVA) program (software version 3.0, National University of Singapore) that measured the caliber of the vessels emerging from the optic disc. The SIVA software automatically detects the optic disc and traces vessels in a zone 0.5 to 2.0-disc diameter from the disc margin. Though the image of FIG. 1 is reproduced in black and white, arterioles can be displayed in a first color (e.g., red) and venules can be displayed in a second color (e.g., blue). The different circular ROIs with various radii around the optic disc center are labeled as B (0.5-1.0 disc diameters away from the disc margin) and C (0.5-2.0 disc diameters away from the disc).

Retinal images can be acquired with, for example, a confocal scanning laser ophthalmoscope (cSLO, EasyScan, iOptics, Netherlands) that is able to acquire high resolution images with, for example, a field of view (FOV) of 45° and image size of 1024×1024 (see FIG. 1). Other FOVs are also valid for this purpose. In some other embodiments, 20 degrees, 100 degrees, 200 degrees, or any other FOV can be applied to the high-resolution images, because advanced imaging provides increased access/visibility of the periphery of the retina. Retinal images from study participants and patients can be masked and collected for further analysis after removing images with poor quality. As used herein, masked refers to the fact that the professional reviewing/ checking the images and conducting the analysis was not aware of the patients' condition and whether the patient was cognitively healthy or had some level of CI. Retinal vessels were segmented with a semi-automated computer-assisted program, Singapore I Vessel Assessment (SIVA, software version 3.0, National University of Singapore). The segmentation quality and vessel classification were inspected using a standardized protocol by a trained grader after the retinal arterioles and venules were identified automatically by the SIVA program. Then, optic-disc centered images of a selected eye from each participant can be skeletonized using the Java image-processing program ImageJ.

Figure 2:
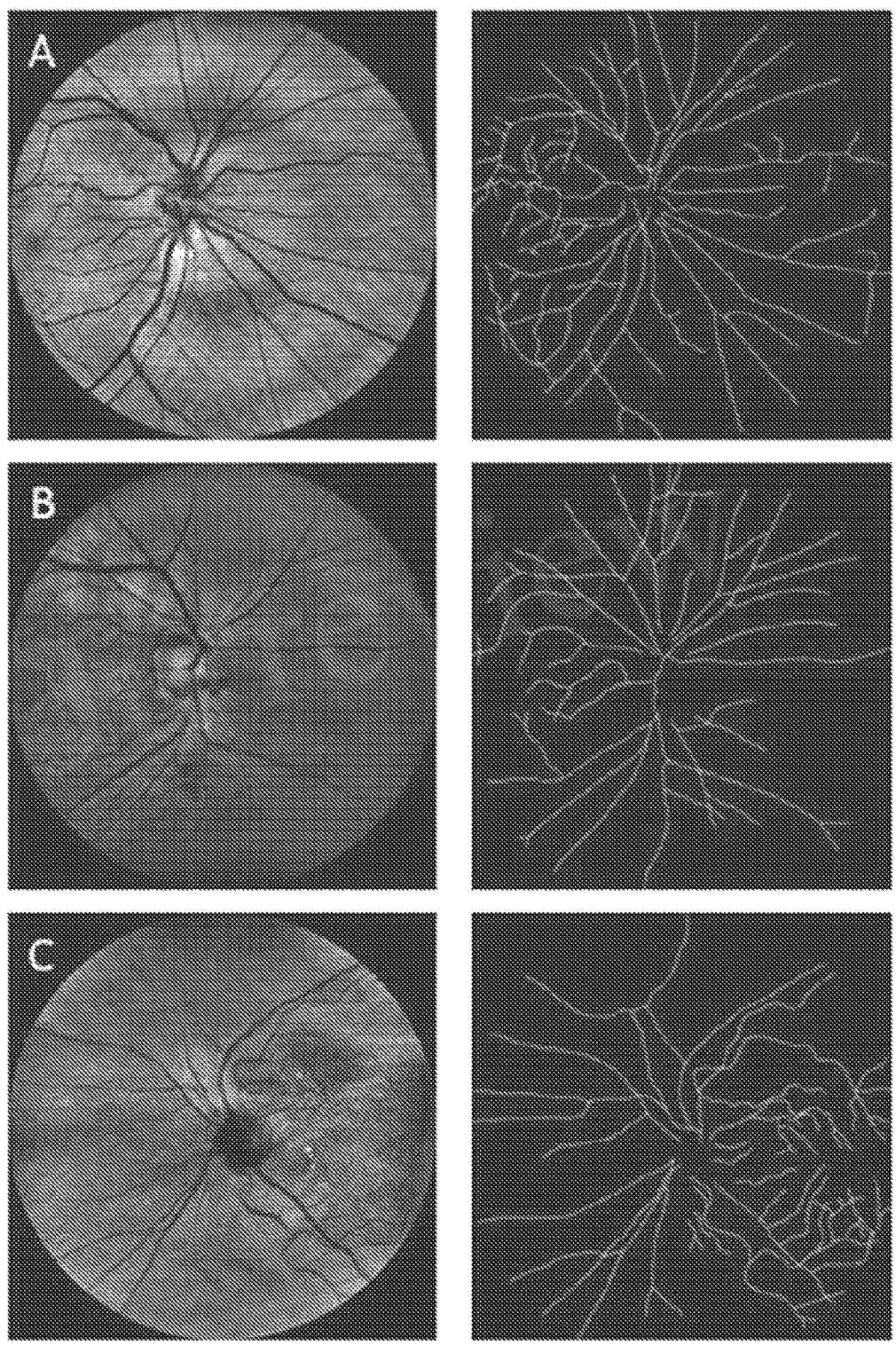
FIG. 2 is a graphical representation of sample images used in fractal analysis of retinal images.

FIG. 2 is a graphical representation of sample images used in fractal analysis of retinal images. Images in the left column of FIG. 2 are the raw images of retinas (e.g., obtained with the EasyScan system), while those in the right are their respective skeleton images that can be used in the fractal analysis. Row A is from a healthy cognitively individual (MoCA score range: 29.6 to 25.2), Row B is from a mild CI (MCI) subject (MoCA score range: 25.2 to 19), and Row C is from a participant with more cognitive deterioration than MCI (MoCA score range: 21 to 11.4). FIG. 2 shows the vasculature network that comprises the whole branching pattern of the associated retina.

Fractal Dimension

The multifractal behavior in the retinal images can be analyzed using the generalized dimension spectrum for q values ranging between −10 and +10, where all dimensions were statistically examined. Accordingly, $D_o$; $D_1$; and $D_2$ can be computed and compared to check for consistency where $D_o > D_1 > D_2$. Because the human retinal vessel structures have been shown to be geometrical multifractals, the vascular FD can be calculated from the skeletonized vascular network (see FIG. 2) using both a monofractal and multifractal approach. In contrast to some preceding studies, the disclosed methods may not need to include different circular regions of interest with various radii around the optic disk centers. Instead, to obtain comparable FD values, the skeleton comprises the whole branching pattern observable in the full 45 degrees FOV.

Fractal analysis is a mathematical method used to measure complexity in natural phenomenon and can characterize the retinal vasculature. The vascular fractal dimension (FD), characterizes a "global" measure that includes the whole branching pattern of the retinal vascular tree. Therefore, a more complex branching pattern indicates a larger FD value. Self-similarity over different scales is an important property of the fractal structures. This self-similar property means that at different magnifications or scales, a similar pattern with different sizes can be perceived. This characteristic of fractal structures can be described by the equation:

$$N(r) = \text{const} \cdot r^{-D} \quad (1)$$

where N(r) is certain measurements applied on the complex pattern of the fractal structure at a scale or magnification r; D is the FD that implies how many new similar patterns are observed as the resolution magnification (scale) increases or decreases.

The FD calculated with the box-counting method is a common monofractal type of FD that used to characterize the human retinal vascular complexity. In this method, the segmented or skeletonized retinal vessels from a retinal fundus or SLO camera are fitted with a rectangular grid consisting of large amount of boxes. The number of boxes in the rectangular grid in this scenario is N(r) with a box having side length r, as shown in Eq. (1). Once a double log plot of the number of boxes N(r) and the box side length r are obtained, the slope of the regression line in this plot indicates the monofractal FD (box counting-based) metric termed $D_o$, as shown in Eq. (2):

$$D_0 = \lim_{r \to 0} \log \frac{Nr}{\log\left(\frac{1}{r}\right)} \quad (2)$$

Because the retinal vessel network geometry has a finer texture or heterogeneity in its space-filling characteristics, its morphological property cannot be described sufficiently by a global parameter reflecting a simple FD obtained by monofractal analysis.

Singularity Spectrum

The human retinal vascular network is considered a geometric multifractal structure characterized by a hierarchy of exponents rather than a single FD as in $D_o$. Therefore, the multifractal property of the human retinal vascular network is characterized by the generalized dimension spectrum (Dq vs q, where Dq represents the FD at the qth order or exponent) and the singularity spectrum (f(α) vs α).

The singularity spectrum of the FD f(a) versus the singularity exponent a is defined as:

$$N(\alpha) = r^{-f(\alpha)} \quad (3)$$

Where N(α) is the number of boxes such that the probability $P_i$ (r) of finding a pixel within a given region i scales as observed in equation 4.

$$P_i = r^{\alpha i} \quad (4)$$

f(α) is hence the FD of all the regions with singularity strengths between α and α+dα where the singularity exponent a takes on values within the interval −∞ and +∞.

The relationship between the D(q) spectrum and the f(α) spectrum is established through the Legendre transformation as seen in equation 5.

$$f(\alpha(q)) = q\alpha(q) - \tau(q) \quad (5)$$

Where α(q) represents the singularity exponent at the qth order moment expressed as:

$$\alpha(q) = d\tau(q)/dq \quad (6)$$

and τ(q) represents the mass correlation exponent of the qth order related to Dq as observed in equation 7.

$$\tau(q) = (q-1)Dq \quad (7)$$

where for q=1, τ(1)=0.

The singularity FD (f(α(q))) and exponent α(q) of the qth order can be computed using, for example, the software Image J together with the FracLac plugin with the settings. Hence, q represents values from −10 to +10 with an increment of 1. These values are computed and then averaged with their standard deviations at each value of q. Then a plot of f(α(q)) versus α(q) with standard deviation error bars is obtained, representing the singularity spectrum. For a multifractal object, the singularity spectrum is typically a parabola with concavity facing down.

Typically, the height (Δf), width (Δα), and asymmetry (A) of the parabola are the measures used to describe the singularity spectrum as seen in equations 8, 9, and 10 below. The α values ($α_0$, $α_1$, $α_2$) of the singularity spectrum at q=0, 1, 2 can also be compared between groups with greater α values indicating greater singularities or maxima and vice versa.

$$\Delta f = f(\alpha)min - f(\alpha)max \tag{8}$$

where f(α)max and f(α)min represent the maximum and minimum f(α) values, respectively.

$$\Delta\alpha = \alpha_{max} - \alpha_{min} \tag{9}$$

Also, $α_{max}$ and $α_{min}$ represent the maximum and minimum α values, respectively. The higher the Δα, the stronger is the multifractality, and the more complex is the pixel distribution within the image.

$$A = (\alpha_0 - \alpha_{min})/(\alpha_{max} - \alpha_0) \tag{10}$$

The parabola of the singularity or F spectrum is symmetric when A=1, left skewed when A>1, and right skewed when A<1. A left skewed F spectrum means that there is a stronger presence of high fractal exponents and a significant fluctuation while a right skewed F Spectrum, on the other hand, posits low fractal exponents and a slight fluctuation.

Lacunarity Analysis

The Λ parameter of the skeletonized images of the participants can be computed with, for example, the Image J software together with the FracLac plugin. The Image J software together with the FracLac plugin computes the Λ parameter based on the variation in pixel density at different box sizes in fixed and sliding scans. A lower Λ parameter indicates more homogeneity of the pixel distribution in the image and vice versa. The mean Λ parameter computed from the Image J software together with the FracLac plugin is then summarized as shown in equation 11.

$$\Lambda = \frac{1}{n}\left(\Sigma_{j=1}^{g}\Sigma_{i=1}^{n}\left[1+\left(\frac{\sigma}{\mu}\right)^{\wedge}2\right]\right) \tag{11}$$

where σ is the standard deviation of the number of pixels that were in a box of size ε; μ is the mean for pixels per box at this size ε, in a box count at an orientation g; and then n is the number of box sizes.

Regional Retina Branching Pattern

Figure 3:
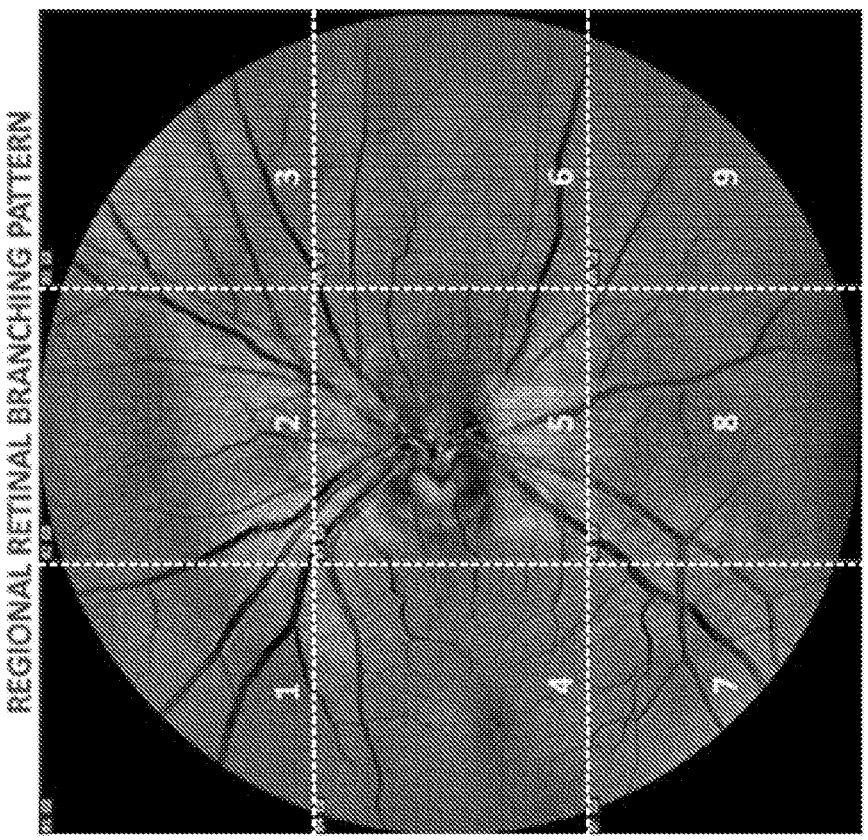
FIG. 3 is a comparison of exemplary retinal images used in whole retina, and regional retinal branching pattern analysis.
Figure 3:
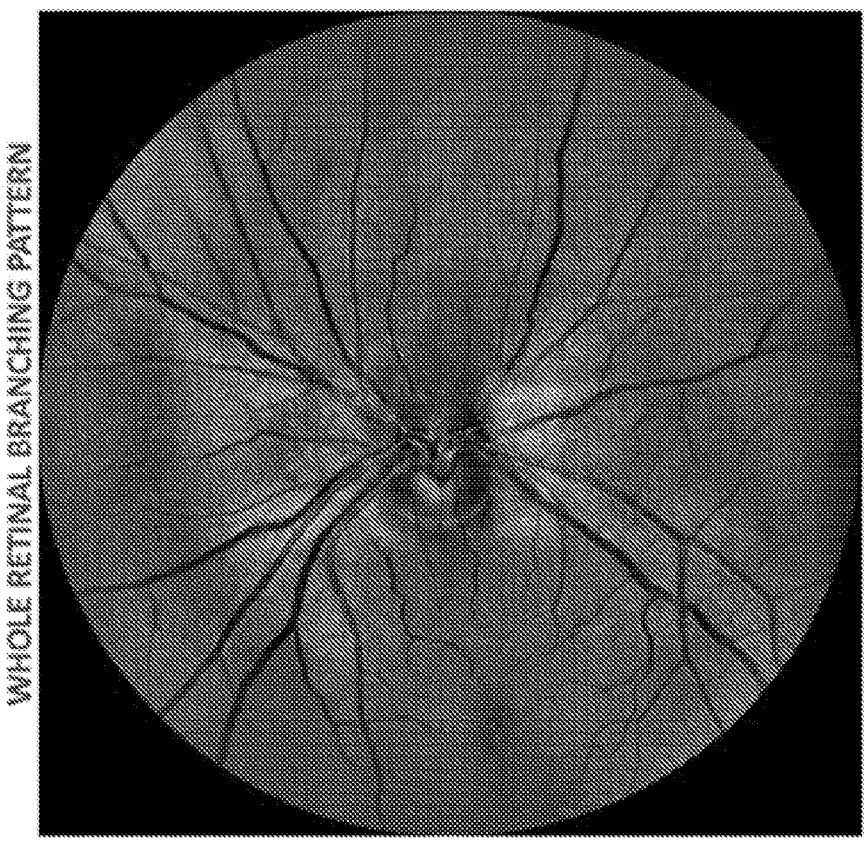

FIG. 3 is a comparison of exemplary retinal images used in whole retina, and regional retinal branching pattern analysis. The images of FIG. 3 are the whole retina displayed on the left, while the right hand image includes an exemplary division of the whole retina (on the left) divided into nine equal regions. For example, the nine regions can include, 1—superotemporal, 2—superior, 3—superonasal, 4—macular, 5—optic disc, 6—nasal, 7—inferotemporal, 8—inferior, and 9—inferonasal.

Retinal images for this portion of the method can be acquired with a confocal scanning laser ophthalmoscope (cSLO, EasyScan, iOptics, Netherlands) that is able to acquire high resolution images with a field of view (FOV) of 45° and image size of 1024×1024. In some implementations, the images can be the same images used for the whole retinal branching pattern, described above in connection with FIG. 1 through FIG. 3. Retinal images from participants can be masked and collected for further analysis after removing images with poor quality. Specifically, retinal vessels were segmented with a semi-automated computer-assisted program, Singapore I Vessel Assessment (SIVA, software version 3.0, National University of Singapore). The segmentation quality and vessel classification were inspected using a standardized protocol by a trained grader after the retinal arterioles and venules were identified automatically by the SIVA program. Then, optic-disc centered images of a selected eye from each participant can be partitioned into nine equal regions observable in the full 45° FOV, and skeletonized using the public domain Java image-processing program ImageJ. FIG. 3 shows the vasculature network that comprised the whole branching pattern as it was obtained for each image and divided into nine equal regions (superotemporal, superior, superonasal, macular, optic disc, nasal, inferotemporal, inferior, inferonasal).

Key Principles

Whole Retinal Branching Pattern

Analysis of combined structural-functional parameters extracted from eye measurements, instead of individual biomarkers, can provide a useful clinical marker of cognitive impairment (CI) that could also provide increased sensitivity and specificity for the differential diagnosis of CI.

Although vessel density analysis can be used to characterize the retinal microvasculature network, the density is not a scale invariant metric (i.e., variations in vessel diameter can alter density), and consequently this fails to be a suitable tool for comparison across dissimilar retinal tissue networks (e.g., microvascular network of a healthy retina vs. diabetic retina). In particular, the complexity of the human retinal microvascular network cannot be precisely quantified using Euclidean geometric parameters because its vascular branching pattern holds a fractal structure characterized by self-similarity and scaling, and it is determined in terms of fractional powers which describe the non-Euclidean shapes. Therefore, combining multifractal analysis along with lacunarity parameter and multifractal spectrum analysis can be used as a more efficient methodology to characterize the vascular network.

This approach also has the advantage of a low-cost implementation in community settings to detect cognitive decline-specific pathology in the retina, which could enable the early diagnosis and monitoring of disease progression Key Principle 1 (Structural-Functional Parameters):

There is a statistical trend pointing to the correlation between retinal neuronal dysfunction and microvasculature changes suggesting that retinal geometric vascular and functional parameters are associated with physiological changes in the retina due to CI. In particular, the Pearson product moment correlation indicates significant associations between the vascular parameters (AVR, LDRt, D0, D1, D2) and IT.

Table 1 below describes the association between retinal vascular measures (i.e., multifractal and lacunarity parameters) and functional measures (ERG IT, ERG amplitude, and MoCA).

TABLE 1

| Parameters | Pearson's correlation (r) | p value |
|---|---|---|
| $\alpha_0$ versus ERG IT | 0.61 | 0.004 |
| $\alpha_1$ versus ERG IT | 0.67 | 0.001 |
| $\alpha_2$ versus ERG IT | 0.71 | <0.001 |
| $\Lambda$ versus ERG IT | −0.51 | 0.022 |
| $\alpha_0$ versus ERG amplitude | 0.41 | 0.07 |
| $\alpha_1$ versus ERG amplitude | 0.35 | 0.13 |
| $\alpha_2$ versus ERG amplitude | 0.29 | 0.22 |
| $\Lambda$ versus ERG amplitude | −0.23 | 0.33 |
| $\alpha_0$ versus MoCA | 0.43 | 0.06 |
| $\alpha_1$ versus MoCA | 0.43 | 0.06 |
| $\alpha_2$ versus MoCA | 0.42 | 0.07 |
| $\Lambda$ versus MoCA | −0.18 | 0.44 |

Specifically, the following trends/outcomes were observed:
- A significant correlation between the 30 Hz flicker ERG implicit time of the b-wave and AVR (artery-vein ratio), D0 (capacity dimension), D1 (information dimension), D2 (correlation dimension); and LDRt (total length to-diameter ratio (i.e., arteriolar+venular); in patients with cognitive decline is intriguing and requires further studies to clarify the underlying pathophysiology and validate its clinical usefulness in predicting the development of cognitive decline using the eye as a surrogate marker. A decrease in amplitude and an increase of the 30 Hz flicker ERG implicit time of the b-wave are usually observed in all retinal pathologies that comprise the photoreceptors when the flicker ERG method has been used to assess photoreceptor function. Also, previous studies suggest only modest decreases in photopigment optical density with age. Therefore, significant correlations between the ERG parameters and vascular measures may be more related to cognitive decline than aging.
- There is a significant positive association between retinal vascular singularity exponents ($\alpha_0$, $\alpha_1$, $\alpha_2$) and the implicit time, which was one of the functional measures obtained with the ERG assessments. In particular, there was a high Pearson correlation coefficient between $\alpha_2$ versus the ERG implicit time. These associations interestingly pointed to a clear perturbation of the neurovascular component as a result of abnormal conditions mediated by the individual's disease status affecting both the brain and eye structures.

A negative association was observed between the $\Lambda$ parameter versus the ERG implicit time. Specifically, the negative association between the $\Lambda$ parameter and the ERG implicit time is expected as FD and $\Lambda$ are hypothesized to be negatively associated.

There were no such associations between $\alpha_0$, $\alpha_1$, $\alpha_2$, and $\Lambda$ versus the ERG amplitude and MoCA, p>0.05.

a. Key Principle 2 (Functional Parameters Obtained with the ERG, CCT and MoCA Tests):

Table 2 lists light-adapted 3.0 flicker ERG (28.3 Hz) measurements recorded from patients with cognitive impairment in comparison with the normative data of the RETeval™ system. Amplitude (µV) and implicit time (ms) are denoted along with the medians and 90% confidence intervals of the 2.5% and 97.5% reference limits. The P values comparing cognitive impairment vs. cognitively healthy cases were calculated by independent sample t test.

TABLE 2

| Light Adapted Test (flicker cone- 3.0 cd · s/m², 30 cd/m², 28.3 Hz) | ERG reference data n = 244 median [90% CI] Age: [76 -86] | Cognitive Impairment Cases n = 20 median [90% CI] Age: [69-90] | Cognitively Healthy Cases n = 19 median [90% CI] Age: [60-88] | p-value |
|---|---|---|---|---|
| Amplitude (µV) | 2.5% limit 19.6 [18-22.1] 97.5% limit 39.4 [35.5-43.1] | 12.6 [10.9-14.4] | 37.4 [36.6-38.2] | <0.001** |
| Implicit Time (ms) | 2.5% limit 25.6 [25.1-26.3] 97.5% limit 29.6 [29.2-29.9] | 31.2 [29.6-32.8] | 29.6 [29.4-29.8] | <0.001** |

**Significant (p < 0.01)

Functional loss in color vision as well as smaller ERG amplitudes and larger peak times were observed in the subjects with CI. As expected the MoCA scores were significantly lower (p<0.001) in the group of cognitive impairment cases compared with the age-matched controls. Specifically, the following trends/outcomes were observed:
- For all full-field ERG measurements, smaller amplitudes and larger peak times were observed in the subjects with cognitive impairment (as shown in Table 2).
- There was a statistically significant (p<0.001) difference in the amplitudes and implicit times between the cognitively healthy group and the one with cognitive deterioration (as shown in Table 2).
- The implicit time was less variable than the amplitude. The implicit time's increase that was perceived with the manifestation of pathologic changes of the retina was highly consistent in all patients with cognitive deterioration, and showed practically no overlap between control data and pathologic values: the range of variation seen for control data is between 29.4 and 29.8 ms, while for patients with cognitive impairment it is between 29.6 and 32.8 ms.
- The fact that the 90% confidence intervals of the averages of the cognitively healthy and cognitively impaired groups are not overlapping (as shown in Table 2) supports the opportunity to define distinctive domains for the values of the implicit time that can be correlated with the presence and, respectively, the non-existence of cognitive impairment in the individuals analyzed.

The visual performance test with the computerized Cone Contrast test (CCT, Innova Systems Inc.) revealed functional loss in color vision, as shown in Table 3.

Table 3 describes long, Middle and Short-CCT scores (i.e., Red, Green and Blue CCT scores) for the cognitive impairment group. CCT scores of 75 or greater are defined as normal (Rabin et al., 2011). The visual performance test with the computerized CCT, revealed functional loss in color vision. The P values were calculated by an independent sample t test.

TABLE 3

| Rabin CCT scores | Cognitive Impairment Cases n = 20 Mean (SD) | Cognitively Healthy Cases n = 19 Mean (SD) | p-value |
|---|---|---|---|
| L-CCT (red) | 56 (12) | 91 (8) | <0.001** |
| M-CCT (green) | 47 (18) | 89 (8) | <0.001** |
| S-CCT (blue) | 63 (12) | 91 (7) | <0.001** |

**Significant ($p < 0.01$)

There were more patients with more green deficiency than red or blue deficiency. The scores corresponding to both groups showed a statistically significance difference. The CCT scores have been reported to be affected in the elderly due to cognitive decline. Not only were most patients with cognitive decline found with more green deficiency than red or blue deficiency, but also all CCT scores were severely reduced below the normal decline level (i.e., below a CCT score of 75) associated with aging and reported for the elderly in the eighth and ninth decades of life (i.e., in the 70-79 and 80-89-year age group). Interestingly, it has been reported that individuals with cognitive deterioration due to AD struggle discriminating between green and blue stimuli on the Stroop test which relies on a cognitive measure that requires intact color vision. These results add to the evidence that extrastriate lesions could result in tritanomalous color deficits, and that the extrastriate cortex is severely disturbed neuropathologically in AD. Therefore, pathological changes due to cognitive decline observed in the striate area (IVcß) of the brain that receives color information from the lateral *geniculate* nucleus, suggest additional basis for deficits in color vision in the brain as described here.

b. Key Principle 3 (Structural Parameters Characterizing Retinal Branching Complexity):

In comparison to age-matched controls shown in Table 4, below, a reduction of vascular branching complexity (FD) in the patients with cognitive decline was observed.

Table 4 lists geometric vascular parameters obtained for patients with cognitive impairment in comparison with the cognitively normal individuals. The data reported was measured in the region C (i.e., area between 0.5 and 2.0 disc diameters away from the disc margin, see FIG. 1) for all parameters except for the fractal parameters that were calculated in the whole area occupied by the branching pattern (FOV=45°). The P values were calculated by independent sample t test.

TABLE 4

| Vascular Parameters | Cognitive Impairment Cases n = 20 Mean (SD) | Cognitively Healthy Cases n = 19 Mean (SD) | p-value |
|---|---|---|---|
| Fractal Dimension | | | |
| $D_0$ | 1.57 (0.06) | 1.61 (0.03) | 0.03* |
| $D_1$ | 1.56 (0.06) | 1.59 (0.03) | 0.03* |
| $D_2$ | 1.55 (0.06) | 1.58 (0.03) | 0.02* |
| Caliber (µm) | | | |
| CRAE | 65.88 (7.39) | 66.73 (6.46) | 0.707 |
| CRVE | 92.54 (7.15) | 92.49 (9.02) | 0.984 |
| Bifurcation | | | |
| BCa | 1.65 (0.46) | 1.47 (0.35) | 0.169 |
| BCv | 1.30 (0.48) | 1.34 (0.49) | 0.812 |
| BCt | 1.55 (0.36) | 1.50 (0.28) | 0.631 |
| AFa | 0.75 (0.11) | 0.74 (0.16) | 0.765 |
| AFv | 0.74 (0.22) | 0.61 (0.19) | 0.042* |
| AFt | 0.77 (0.05) | 0.71 (0.10) | 0.018* |
| Tortuosity | | | |
| cTORTa ($10^{-4}$) | 4.30 (7.04) | 4.13 (0.83) | 0.485 |
| cTORTv ($10^{-4}$) | 4.06 (1.06) | 3.82 (0.80) | 0.433 |
| cTORTt ($10^{-4}$) | 4.17 (0.71) | 3.97 (0.64) | 0.374 |
| Ratio measures | | | |
| AVR | 0.92 (0.25) | 0.86 (0.20) | 0.427 |
| LDRa | 8.98 (7.46) | 7.35 (5.86) | 0.456 |
| LDRv | 4.52 (6.06) | 2.58 (3.77) | 0.240 |
| LDRt | 9.7 (6.8) | 7.13 (4.56) | 0.173 |

AVR, arteriole-venular ratio; BCa, arteriolar branching coefficient; BCv, venular branching coefficient; BCt total branching coefficient (i.e., arteriolar + venular); CRAE, central retinal arteriolar equivalent; CRVE, central retinal venular equivalent; LDRa, arteriolar length-to-diameter ratio; LDRv, venular length-to-diameter ratio; LDRt, total length-to-diameter ratio (i.e., arteriolar + venular); cTORTa, curvature arteriolar tortuosity cTORTv, curvature venular tortuosity; cTORTt, total tortuosity (i.e., arteriolar + venular); AFa, asymmetry arteriolar factor; AFv, asymmetry venular factor; Aft, total asymmetry factor (i.e., arteriolar + venular). $D_0$: capacity dimension, $D_1$: information dimension, $D_2$: correlation dimension.
*Significant ($p < 0.05$)

The disclosed methods provide a robust approach that considers the actual multifractal properties of the retinal microvasculature network. Of note, since the findings of AMD and cognitive deterioration due to AD commonalities suggest a degree of overlap, we assessed all retinal images to identify and rule out retinal pathological features related to AMD. Specifically, the following trends/outcomes were observed:

The vascular fractal dimension was lower in individuals with CI (capacity, information and correlation dimensions: D0, D1; and D2 (mean±SD): 1.57±0.06; 1.56±0.06; 1.55±0.06; age: 81±6 years) vs. controls (1.61±0.03; 1.59±0.03; 1.58±0.03; age: 80±7 years).

Figure 6:
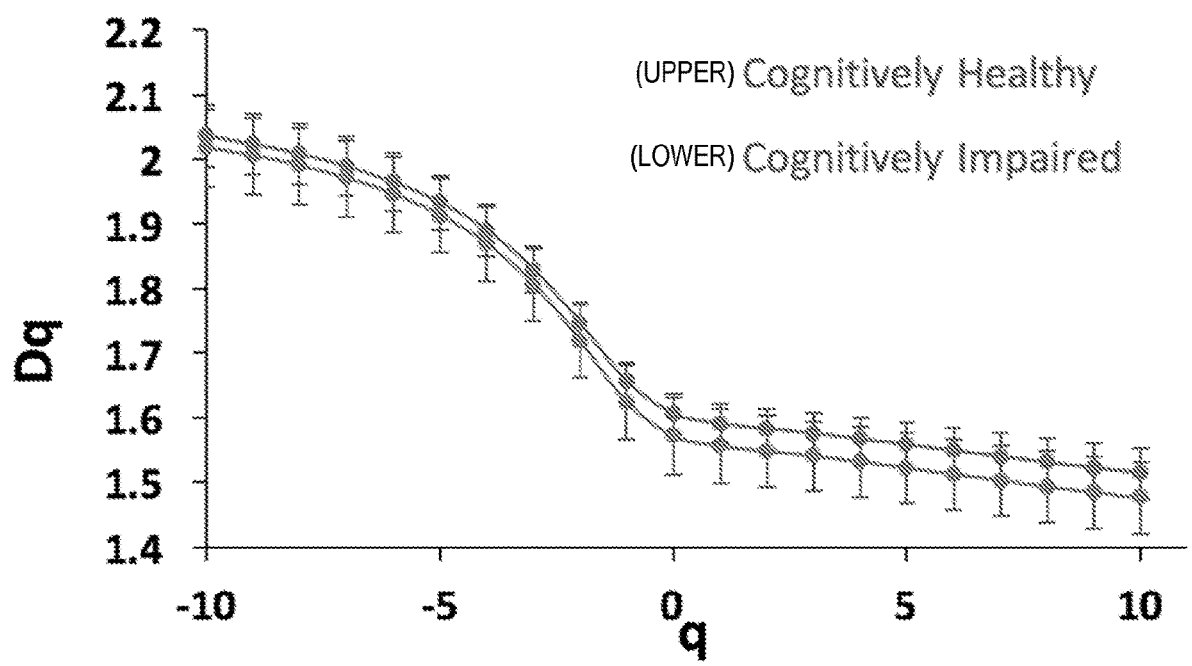
FIG. 6 is a plot diagram of generalized dimension spectrum Dq vs. q for the cognitively healthy individuals and cognitively impaired individuals.

The vascular tree of the whole retinal branching pattern displayed multifractal properties revealed by the descending sigmoid curve. The calculated mean and standard deviations of generalized dimensions D0, D1, and D2 for both groups are shown in Table 4, above. The sigmoid curve is shown in FIG. 6. FIG. 6 is a plot diagram of generalized dimension spectrum Dq vs. q for the cognitively healthy individuals (n=19, bottom trace) and cognitively impaired individuals (n=20, top trace).

The α values ($\alpha_0$, $\alpha_1$, $\alpha_2$) of the singularity spectrum at q=0, 1, 2 were significantly greater in the cognitively healthy participants than in the cognitively impaired participants, with greater than moderate Cohen's d or effect size for $\alpha_0$ and $\alpha_1$ (d=0.63, 0.63, respectively), and a large Cohen's d for $\alpha_2$ (d=0.97), as shown in Table 5, below. Thus, the participants with CI had lower singularity or α values compared to the cognitively healthy participants and this difference had a high effect size for $\alpha_2$ but not $\alpha_0$ and $\alpha_1$.

A significantly lower singularity (i.e., reduced singularity spectrum exponents ($\alpha_0$, $\alpha_1$, $\alpha_2$)) was found in the participants with CI compared to the cognitively healthy participants with a large effect size difference for $\alpha_2$ (shown in Table 5, below), which may indicate that the reduced retinal vascular branching complexity for patients with CI, possibly due to reduced retinal neural demand, could be incorporated as a clinical tool for the diagnosis of CI. The neurovascular coupling concept of the retina calls for increased vascular demand with associated increased neural activity.[53, 54] It is well established that the neurodegeneration that occurs in the brain of patients with CI is associated with loss of retinal ganglion cells.[10,11] This trend implies that there will be reduced vascular demand in terms of nutrients and oxygen from the retinal neurons in these subjects and a potential remodeling of the branching pattern complexity of the retinal vessels in these subjects. This tendency may explain the significantly reduced singularity spectrum exponents as well as a trend towards lower maxima in the subjects with CI versus the age- and sex-matched cognitively healthy controls.

The $\Lambda$ parameter was not significantly different between the participants with CI and the cognitively healthy participants (shown in Table 5, below).

Table 5 Multifractal and Lacunarity parameters (mean±SD) obtained for the cognitively impaired and cognitive healthy participants.

TABLE 5

| Multifractal and lacunarity parameters | Cognitively impaired group | Cognitively healthy group | p value | Cohen's d |
|---|---|---|---|---|
| $\alpha_0$ | 1.60 ± 0.06 | 1.63 ± 0.03 | 0.03 | 0.63 |
| $\alpha_1$ | 1.56 ± 0.06 | 1.59 ± 0.03 | 0.03 | 0.63 |
| $\alpha_2$ | 1.54 ± 0.05 | 1.58 ± 0.03 | 0.02 | 0.97 |
| $\Delta f$ | 0.87 ± 0.10 | 0.87 ± 0.07 | 0.93 | NA |
| $\Delta\alpha$ | 0.74 ± 0.05 | 0.71 ± 0.05 | 0.14 | NA |
| $A^a$ | 0.35 ± 0.06 | 0.35 ± 0.05 | 0.99 | NA |
| $\Lambda$ | 0.35 ± 0.05 | 0.34 ± 0.03 | 0.48 | NA |

Note:
$\alpha_0$, $\alpha_1$, and $\alpha_2$ represent the singularity exponents at q = 0, 1, 2, respectively. The $\Delta f$, $\Delta\alpha$, and A represent the height, width, and asymmetry of the singularity spectrum, respectively. The $\Lambda$ parameter represents lacunarity, indicating the gap dispersion within the image.
$^a$Mann-Whitney U-test was performed, otherwise an independent sample t-test was performed.

C. Key Principle 4 (Structural Parameters Characterizing Retinal Branching Morphology and Features):

The asymmetry factor, a structural parameter, was significantly higher in patients with cognitive impairment than in age-matched controls, as shown in Table 4 above. Peripheral drusen-like regions and retinal pigment dispersion were noted in some elderly subjects with MCI.

Figure 7:
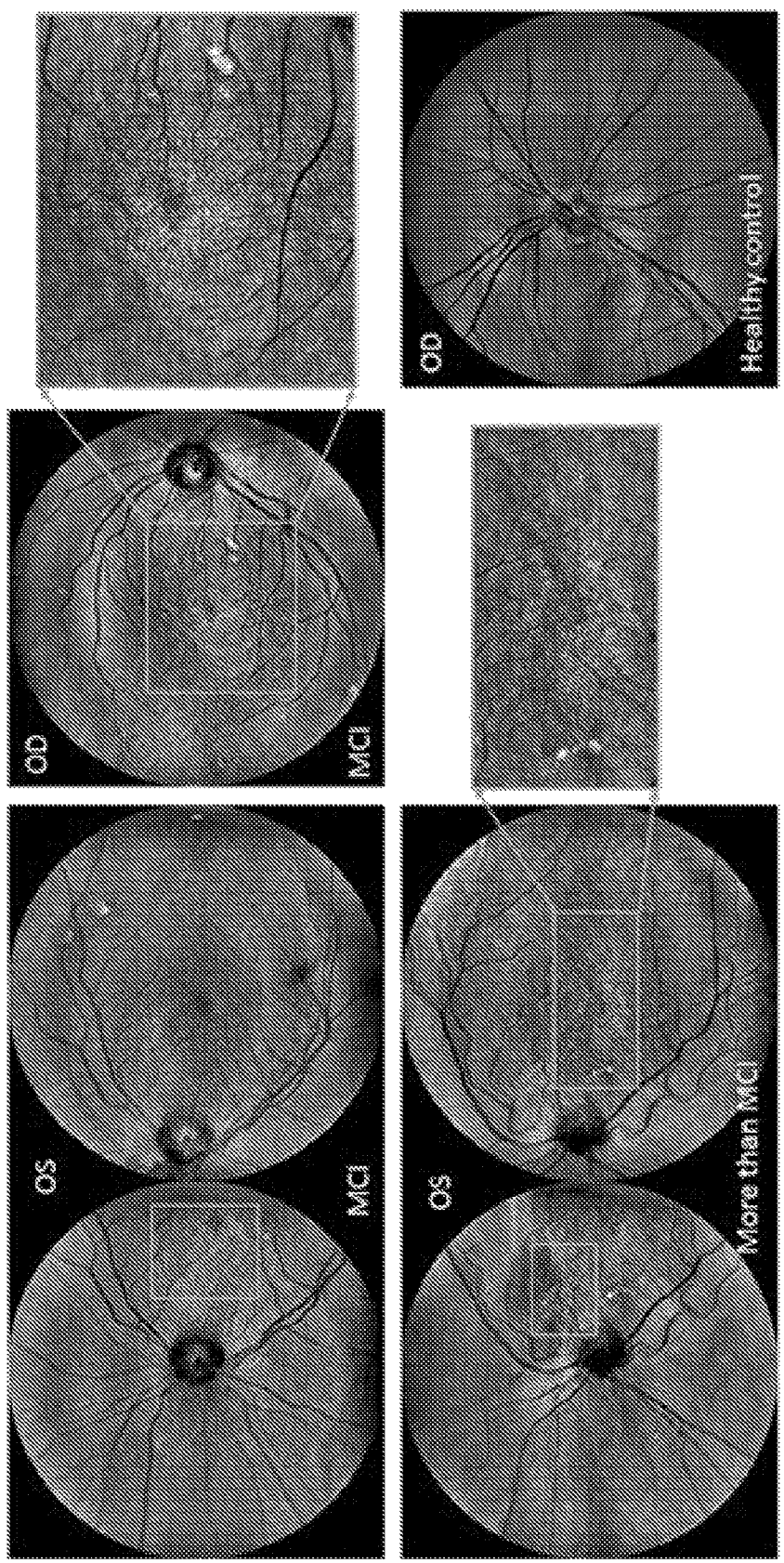
FIG. 7 is a graphical representation of an exemplary retinal topographical features observed in individuals with mild cognitive impairment.

FIG. 7 is a graphical representation of an exemplary retinal topographical features observed in individuals with mild cognitive impairment. Top row: Central and nasal infrared light-images obtained from a female subject (79 years old) with MCI showing extramacular features such as drusen-like regions depicted by irregularly shaped bright spots in the periphery of the superior quadrant as well as with pigment dispersion in both eyes. Bottom image: Left—Central and nasal infrared light-images obtained from a female subject (81 years old) with MCI showing tortuous vessels, extramacular features such as drusen-like regions along with pigment dispersion in the left eye. Right—Nasal infrared-light image obtained from a healthy control (71 years old). All images were acquired with the EasyScan Unit (i-Optics Corporation, The Netherlands). The EasyScan camera is a dual color confocal SLO: Infrared (785 nm) and pure green (532 nm). The different colors are related to different penetration depth. The red arrows indicate the location of the drusen and white spots observed at extramacular locations. The ROIs enclosed by the orange rectangles indicate the locations where pigment dispersion was observed. The green light-image (see fundus image shown in FIG. 1) is reflected at the retinal nerve fiber layer showing the vascular structure up to the 4th bifurcation. The infrared light-image is reaching the choroidal vessel layer.

Interestingly, extramacular drusen in the superior quadrant was observed for some MCI individuals. This trend has been reported previously as to be significantly related with cognitive deterioration due to AD in patients with peripheral drusen. Two earlier studies that may add to this evidence have described the presence of amyloid beta in retinal drusen deposits. Also, abundant amyloid beta pathology has been detected in AD patients in the periphery of the superior quadrant.

Regional Retina Branching Pattern

Statistical significance was only observed for the optic disc and macula regions. As in the whole retina branching pattern, the analysis of combined structural-functional parameters extracted from eye measurements, instead of individual biomarkers, may provide a useful clinical marker of cognitive impairment (CI) that could also provide increased sensitivity and specificity for the differential diagnosis of CI. This approach also has the advantage of a low-cost implementation in community settings to detect cognitive decline-specific pathology in the retina, which could enable the early diagnosis and monitoring of disease progression a. Key Principle 1 (Structural-Functional Parameters):

Table 6 lists various associations between retinal multifractal and functional parameters. P-values of less than 0.001 are represented as <0.001. ‡Indicates a significant strong correlation ($|r|\geq 0.7$). *Indicates a significant moderate correlation ($|r|>0.55$). †Indicates a significant modest correlation (r from 0.32 to 0.55).

The generalized dimensions ($D_o$, $D_1$, $D_2$) and singularity spectrum ($\alpha_o$, $\alpha_1$, $\alpha_2$) values were significantly associated with MoCA scores and IT in the macular region (positive correlation), but these associations were absent in the optic disc region (Table 6). Also, the associations with the MoCA scores were absent in the whole retinal branching pattern. Moreover, a significant negative correlation between the lacunarity parameter with the ERG-implicit time parameter was only observed when considering the whole retinal branching pattern. Overall, the analyses revealed moderate ($|r|>0.55$) and strong ($|r|\geq 0.7$) correlation coefficients in the correlations found for the generalized dimensions ($D_o$, $D_1$, $D_2$) and singularity spectrum ($\alpha_o$, $\alpha_1$, $\alpha_2$) vs. IT parameters in the whole retina and macular region. Also, a modest correlation ($|r|$ between 0.32 to 0.55) was obtained between the lacunarity parameter with the ERG-implicit time parameter in the whole retina (Table 6). In particular, the correlations obtained between the generalized dimensions ($D_o$, $D_1$, $D_2$) and the ERG-implicit time parameter were higher in the macula region.

TABLE 6

| Parameters Correlated | Optic Disc Region (Pearson coefficients, p-value) | Macular Region (Pearson coefficients, p-value) | Whole Retina (Pearson coefficients, p-value) |
|---|---|---|---|
| Multifractal Dimension Parameters | | | |
| $D_0$ vs. MoCA | r = 0.22, p = 0.35 | †r = 0.47, p = 0.04 | r = 0.43, p = 0.06 |
| $D_1$ vs. MoCA | r = 0.21, p = 0.37 | †r = 0.46, p = 0.04 | r = 0.43, p = 0.06 |
| $D_2$ vs. MoCA | r = 0.21, p = 0.38 | †r = 0.45, p = 0.04 | r = 0.42, p = 0.06 |
| $D_0$ vs. IT | r = 0.40, p = 0.08 | *r = 0.69, p = 0.001 | *r = 0.64, p = 0.002 |
| $D_1$ vs. IT | r = 0.39, p = 0.09 | *r = 0.69, p = 0.001 | *r = 0.67, p = 0.001 |
| $D_2$ vs. IT | r = 0.40, p = 0.08 | ‡r = 0.70, p = 0.001 | *r = 0.69, p = 0.001 |
| $f(\alpha)$ Spectrum Parameters | | | |
| $\alpha 0$ vs. MoCA | r = 0.22, p = 0.34 | †r = 0.46, p = 0.04 | r = 0.43, p = 0.06 |
| $\alpha_1$ vs. MoCA | r = 0.21, p = 0.37 | †r = 0.46, p = 0.04 | r = 0.43, p = 0.06 |
| $\alpha_2$ vs. MoCA | r = 0.20, p = 0.39 | †r = 0.44, p = 0.05 | r = 0.42, p = 0.07 |
| $\alpha_0$ vs. IT | r = 0.43, p = 0.06 | *r = 0.69, p = 0.001 | *r = 0.61, p = 0.004 |
| $\alpha_1$ vs. IT | r = 0.39, p = 0.09 | *r = 0.69, p = 0.001 | *r = 0.67, p = 0.001 |
| $\alpha_2$ vs. IT | r = 0.42, p = 0.07 | *r = 0.69, p = 0.001 | ‡r = 0.71, p < 0.001 |
| Lacunarity Parameters | | | |
| $\Lambda$ vs. MoCA | r = −0.25, p = 0.28 | r = −0.24, p = 0.30 | r = −0.18, p = 0.44 |
| $\Lambda$ vs. IT | r = −0.07, p = 0.77 | r = −0.31, p = 0.19 | †r = −0.51, p = 0.022 |

The generalized dimensions ($D_o$, $D_1$, $D_2$) and singularity spectrum ($\alpha_o$, $\alpha_1$, $\alpha_2$) values were significantly associated with MoCA scores and ERG-implicit time in the macular region (positive correlation), but these associations were absent in the optic disc region, as shown in Table 6.

The associations with the MoCA scores were absent in the whole retinal branching pattern, as shown in Table 6.

A significant negative correlation between the lacunarity parameter with the ERG-implicit time parameter was only observed when considering the whole retinal branching pattern. The analyses revealed moderate ($|r|>0.55$) and strong ($|r|\geq 0.7$) correlation coefficients in the correlations found for the generalized dimensions ($D_o$, $D_1$, $D_2$) and singularity spectrum ($\alpha_o$, $\alpha_1$, $\alpha_2$) vs. IT parameters in the whole retina and macular region, as shown in Table 6.

According to the Receiver Operating Characteristic (ROC) analysis, the overall predictive accuracy of the multimodal ($D_o$, $D_1$, $D_2$, $\alpha_o$, $\alpha_1$, $\alpha_2$, $\Lambda$, IT) metric in discriminating patients with cognitive impairment from cognitively healthy subjects may be better (Area Under the Curve (AUC)~0.95) than that of the other combined measurements AUC range~[0.73-0.88]. The ROC is a graphical plot that illustrates the diagnostic ability of a binary classifier system as its discrimination threshold is varied.

The analyses performed in sectoral regions of the retina uncovered significant differences in patients with CI that were masked in the analysis considering the whole retinal branching pattern.

The sectoral region analysis captured better the pattern alterations of both the neural function and locally low-dimensional regions (i.e., areas with reduced complexity). This trend indicates that the functional variation is occurring from a space-filling microvasculature network which nurtures the retina to a less dense microvasculature network as it degenerates in subjects with CI. This approach is expected to be especially useful for assessing subtle differences or pathologies in the retinal function and microvasculature network morphology of elderly subjects at risk of cognitive decline. Therefore, these results demonstrate the advantage of our quantitative approach compared to the prior analysis for which only the generalized dimensions were used when considering the whole retinal branching pattern.

The higher degree of "gappiness" observed in the retinal vasculature network of individuals with CI was only significantly different from the HC individuals in the optic nerve head region. This result may be an indication of decreased (collateral) circulation in this region with lower asymmetry caused by vessel remodeling showing a more available space between them indicating a less effective neurovascular coupling that could be related to the reduced vascular demand in terms of nutrients and oxygen from the retinal neurons and the typical thinning of the peripapillary retinal nerve fiber layer reported in AD and other dementia related studies due to the loss of retinal ganglion cells. Interestingly, the neurovascular coupling dysfunction was also characterized by the large effect size found for the associations between the generalized dimensions and multifractal spectrum values with the ERG-implicit time in both the macular region and whole retina. These associations intriguingly pointed to a clear perturbation of the neurovascular component as a result of abnormal conditions mediated by the individual's disease status affecting both the brain and eye structures. Also, besides the microcirculatory dysfunction and provided that the optic nerve is surrounded by cerebrospinal fluid which flows through paravascular spaces that surround small perforating pial vessels, the observed higher degree of "gappiness" in the optic nerve might be associated to an underlying neuroinflammation process. However, further investigation is required to find whether or not the lacunarity can reflect the biology of inflammation in AD and other related dementia conditions, and play an important role in the development of cognitive decline.

While the prior analyses suggested that the small sample size of our study may have accounted for masked alterations in patients with cognitive impairment in the analysis when considering the whole retinal branching pattern, the sectoral region analyses show that the sample size did not affect the significant difference and large effect size found for the retinal vascular FD parameters, lacunarity and multifractal spectra values between the two groups as well as the associations between the retinal vascular and functional parameters.

b. Key Principle 2 (Structural Parameters Characterizing Retinal Branching Complexity):

Table 7. Multifractal dimension parameters and lacunarity values (mean±SD) of study participants with CI and cognitively healthy subjects for the analyses considering the regional and whole retinal branching pattern. *Mann Whitney U test was performed; otherwise independent t test was performed. Abbreviations: Generalized dimensions ($D_0$, $D_1$, $D_2$) and lacunarity ($\Lambda$), NA: not applicable. Cohen's d was not computed in the absence of statistical significance.

A multifractal organization has been shown for the retinal microvasculature network. Likewise, the multifractal behavior satisfied the $D_0 > D_1 > D_2$ criteria for both groups in the skeletonized images of the optic disc and macular regions as well as in the whole retina, demonstrating the multifractal nature of the retinal vessel network. Statistical significance was only observed for the optic disc and macula regions. Therefore, results are only reported for these two regions (Table 7). The $D_0$, $D_1$ and $D_2$ values in the cognitively healthy group were significantly greater in the optic disc region vs. participants with CI ($p<0.05$); respectively (Table 7).

TABLE 7

| Multifractal Dimension Parameters | Cognitively Healthy Participants (n = 19) | | | Cognitively Impaired Participants (n = 20) (p-value, Cohen's d) | | |
|---|---|---|---|---|---|---|
| | Optic Disc | Macular | Whole Retina | Optic Disc | Macular | Whole Retina |
| $D_0$ | 1.59 ± 0.05 | 1.50 ± 0.09 | 1.61 ± 0.03 | 1.52 ± 0.08 (0.006, 1.05) | 1.44 ± 0.16 (0.11, NA) | 1.57 ± 0.06 (0.03, 0.84) |
| $D_1$ | 1.57 ± 0.05 | 1.48 ± 0.09 | 1.59 ± 0.03 | 1.50 ± 0.08 (0.005, 1.05) | 1.42 ± 0.15 (0.14, NA) | 1.56 ± 0.06 (0.03, 0.63) |
| $D_2$ | 1.56 ± 0.05 | 1.46 ± 0.08 | 1.58 ± 0.03 | 1.49 ± 0.08 (0.004, 1.05) | 1.41 ± 0.15 (0.15, NA) | 1.55 ± 0.06 (0.02, 0.63) |
| $\Lambda$ | 0.31 ± 0.02 | 0.32 ± 0.05 | 0.34 ± 0.03 | 0.33 ± 0.04 (0.03, 0.63) | 0.32 ± 0.06 (0.73, NA)* | 0.35 ± 0.05 (0.48, NA) |

Table 8. Singularity spectrum parameters (mean±SD) of study participants with CI and cognitively healthy subjects for the singularity spectrum analysis considering the regional and whole retinal branching pattern. *Mann Whitney U test was performed; otherwise independent t test was performed. Abbreviations: Singularity exponents ($\alpha_0$, $\alpha_1$, $\alpha_2$) of the F spectrum at q=0, 1, 2, respectively. The $\Delta f$, $\Delta \alpha$, and A represent the height, width, and asymmetry of the singularity spectrum, respectively. NA: not applicable. Cohen's d was not computed in the absence of statistical significance. Table 8 (below) shows similar trends in the optic disc region for $\alpha_0$, $\alpha_1$, $\alpha_2$ in the $f(\alpha)$ for the cognitively healthy group vs. participants with CI ($p<0.05$); respectively. Also, similar trends were obtained for the generalized dimensions (Dq) and singularity spectrum ($f(\alpha)$) analyses in the whole retinal branching pattern but the effect size (d) for the optic disc region was greater when compared with the whole retinal branching pattern (d=1.05 vs. 0.84, Table 7). Lacunarity values were greater for participants with CI than controls, p=0.03 in the optic disc region but this difference was absent in the whole retinal branching pattern and macular region, p=0.48 and p=0.73; respectively (Table 7).

TABLE 8

| Singularity Spectrum Parameters | Cognitively Healthy Participants (n = 19) | | | Cognitively Impaired Participants (n = 20) (p-value) | | |
|---|---|---|---|---|---|---|
| | Optic Disc | Macular | Whole Retina | Optic Disc | Macular | Whole Retina |
| $\alpha_0$ | 1.63 ± 0.05 | 1.55 ± 0.09 | 1.63 ± 0.03 | 1.57 + 0.08 (0.01, 0.90) | 1.47 ± 0.17 (0.18, NA)* | 1.60 ± 0.06 (0.03, 0.63) |
| $\alpha_1$ | 1.57 ± 0.05 | 1.48 ± 0.09 | 1.59 ± 0.03 | 1.50 ± 0.08 (0.005, 1.05) | 1.42 ± 0.15 (0.14, NA) | 1.56 ± 0.06 (0.03, 0.63) |
| $\alpha_2$ | 1.55 ± 0.05 | 1.45 ± 0.08 | 1.58 ± 0.03 | 1.48 ± 0.08 (0.004, 1.05) | 1.40 ± 0.14 (0.15, NA) | 1.54 ± 0.05 (0.02, 0.97) |

TABLE 8-continued

| | Cognitively Healthy Participants (n = 19) | | | Cognitively Impaired Participants (n = 20) (p-value) | | |
|---|---|---|---|---|---|---|
| Singularity Spectrum Parameters | Optic Disc | Macular | Whole Retina | Optic Disc | Macular | Whole Retina |
| A | 0.34 ± 0.07 | 0.42 ± 0.08 | 0.35 ± 0.05 | 0.37 ± 0.09 (0.36, NA) | 0.38 ± 0.15 (0.29, NA) | 0.35 ± 0.06 (0.99, NA)* |
| $\Delta\alpha$ | 0.92 ± 0.10 | 0.94 ± 0.11 | 0.71 ± 0.05 | 0.95 ± 0.08 (0.51, NA)* | 0.92 ± 0.14 (0.55, NA) | 0.74 ± 0.05 (0.14, NA) |
| $\Delta f\alpha$ | 1.05 ± 0.12 | 1.01 ± 0.13 | 0.87 ± 0.07 | 1.02 ± 0.12 (0.65, NA)* | 1.06 ± 0.19 (0.37, NA) | 0.87 ± 0.10 (0.93, NA) |

The $D_0$, $D_1$ and $D_2$ values in the cognitively healthy group were significantly greater in the optic disc region vs. participants with CI (p<0.05); respectively (Table 7).

Similar trends were obtained in the optic disc region for $\alpha_0$, $\alpha_1$, $\alpha_2$ in the f($\alpha$) for the cognitively healthy group vs. participants with CI (p<0.05); respectively (Table 8). In particular, the values of $\alpha_0$, $\alpha_1$, and $\alpha_2$ were significantly greater in the cognitively healthy participants than in the cognitively impaired participants in the optic disc region, with greater than moderate Cohen's d or effect size for $\alpha_0$ and $\alpha_1$ (d=0.90 vs. 0.63, and 1.05 vs. 0.63, respectively), and a large Cohen's d for $\alpha_2$ (d=1.05 vs. 0.97). Although as noted above, similar trends were obtained for the generalized dimensions (Dq) and singularity spectrum (f($\alpha$)) analyses in the whole retinal branching pattern, the effect size (d) for the optic disc region was greater when compared with the whole retinal branching pattern (d=1.05 vs. 0.84).

Lacunarity values were greater for participants with CI than controls, p=0.03 in the optic disc region but this difference was absent in the whole retinal branching pattern and macular region, p=0.48 and p=0.73; respectively (Table 7).

While the lacunarity parameter in individuals with CI, as a measure of the texture or coarseness of fractals, was only significantly higher in the optic disc region which is constituted by the axons of the retinal ganglion cells, the generalized dimensions and singularity spectrum parameters were significantly smaller in both the optic disc and whole retina of subjects with CI compared to HC. These results demonstrated that the reduced complexity of the retinal structure might be associated to CI decline.

Vascular patterns in a sectoral region with lower fractal dimension are characterized by higher lacunarity and shift of the singularity spectrum towards a lower a range and lower maxima in comparison to vascular patterns with smaller lacunarity. These results were in place for patients with CI suggesting a reduction of blood flow efficiency and impairment in the microcirculatory transport due to a reduction from optimal microvascular network architecture.

c. Key Principle 3 (Structural Parameters Characterizing Retinal Branching Morphology and Features):

Provided the same data was used in this analysis, as in the study considering the whole branching pattern, peripheral drusen-like regions and retinal pigment dispersion were noted in some elderly subjects with MCI. Interestingly, extramacular drusen in the superior quadrant was observed for some MCI individuals.

Figure 4:
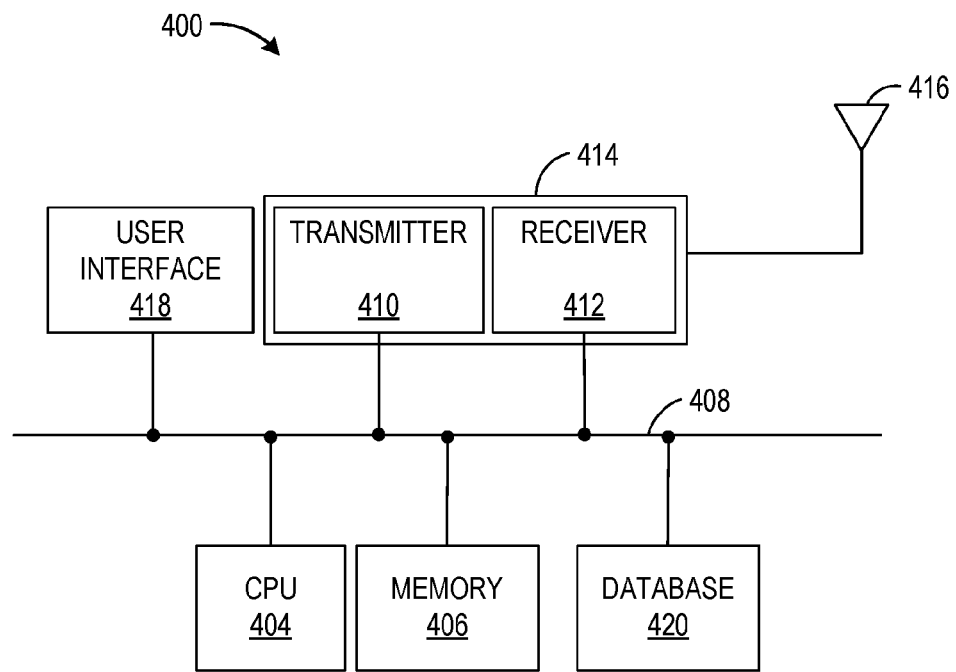
FIG. 4 is a functional block diagram of an embodiment of a device for diagnosing cognitive impairment in a patient.

FIG. 4 is a functional block diagram of an embodiment of a device for diagnosing cognitive impairment in a patient. A device 400 can be configured to implement the various methods described herein.

The device 400 can include one or more processors or processor units (processor) 204. The processor 404 can control operation of the device 400. The processor 404 can also be referred to herein as a central processing unit (CPU). The processor 404 can include or be a component of a processing system implemented with one or more processors 404. The one or more processors 404 can be implemented with any combination of general-purpose microprocessors, microcontrollers, neural processing units (NPUs), digital signal processors (DSPs), field programmable gate array (FPGAs), programmable logic devices (PLDs), controllers, state machines, gated logic, discrete hardware components, dedicated hardware finite state machines, or any other suitable entities that can perform calculations or other manipulations of information. The processors 204 can also perform quantum computing functions.

The device 400 can also have a memory 406 coupled to the processor 404. The memory 406 can include both read-only memory (ROM) and random access memory (RAM). The memory 406 can provide instructions and data to the processor 404.

At least a portion of the memory 406 can also include non-volatile random access memory (NVRAM). The processor 404 can perform logical and arithmetic operations based on program instructions stored within the memory 406. The instructions in the memory 406 can be executable to implement the methods described herein. The processor 404 and the memory 406 can also include machine-readable media for storing software. Software shall be construed broadly to mean any type of instructions, whether referred to as software, firmware, middleware, microcode, hardware description language, machine learning, AI, or otherwise. Instructions can include code (e.g., in source code format, binary code format, executable code format, or any other suitable format of code). The instructions, when executed by the one or more processors, cause the processing system to perform the various functions described herein.

The device 400 can also include a transmitter 410 and/or a receiver 412 to allow transmission and reception of data between the device 400 and a remote location. The transmitter 410 and the receiver 412 can be combined into a transceiver 414. The device 400 can also have one or more antennas 416 electrically coupled to the transceiver 414. The device 400 can also include (not shown) multiple transmitters, multiple receivers, multiple transceivers, and/or multiple antennas as needed for various communication standards.

The device 400 can have a communications bus 408 communicatively coupling the various components of the device 400. The communications bus 408 can also be coupled to an external or wide area network (WAN) such as the Internet.

The transmitter 410 can be configured to transmit packets having different packet types or functions. For example, the transmitter 410 can be configured to transmit packets of different types generated by the processor 404. For example, the processor 404 can be configured to determine the type of packet and to process the packet and/or fields of the packet accordingly. The processor 404 can be configured to generate a discovery packet including a discovery message, beacon, or other information, and to determine what type of packet information to use in a particular instance.

The receiver 412 can be configured to receive packets or other information having different packet types. In some examples, the receiver 412 can be configured to detect a type of a packet used and to process the packet accordingly.

In some embodiments, the transmitter 410 and the receiver 412 can be configured to transmit and receive information via other wired or wireline systems or means to and from the user device 202 via the communications bus 408 or wirelessly via the antenna 216.

The device 400 can further include a user interface 418. The user interface 418 or UI 418 can include a keypad, a microphone, a speaker, and/or a display. The user interface 418 can include any element or component that conveys information to a user of the device 400 and/or receives input from the user. The user interface 418 can be used to listen to or otherwise receive verbal questions, statements, or commands from a user. The user interface 418 can further include one or more speakers to project sounds, such as speech or other noises from the doll 100. In some embodiments, the user interface 418 can be provided or otherwise displayed at the user device 202.

The device 400 can further communicate with the sensors 120. The sensors 120 can be multiple small sensors distributed about the doll 100 or can be fewer large sensors covering large portions of the body as needed. In some embodiments, the sensors 120 can receive power from the power supply 208 as needed.

The device can be coupled to a database 420. The database 420 can receive and store data related to C in a population. The database 420 can store, for example, a plurality of retinal images, skeletonized retinal images, ERG data/metrics, calculations for FD, singularity spectrum, lacunarity, and other data related to the methods disclosed herein. The data stored in the database 420 can serve as baseline or reference data that can be used to determine C in a given patient. Such comparisons can be based on one or more functional and structural measures of a retina, as described above.

Figure 5:
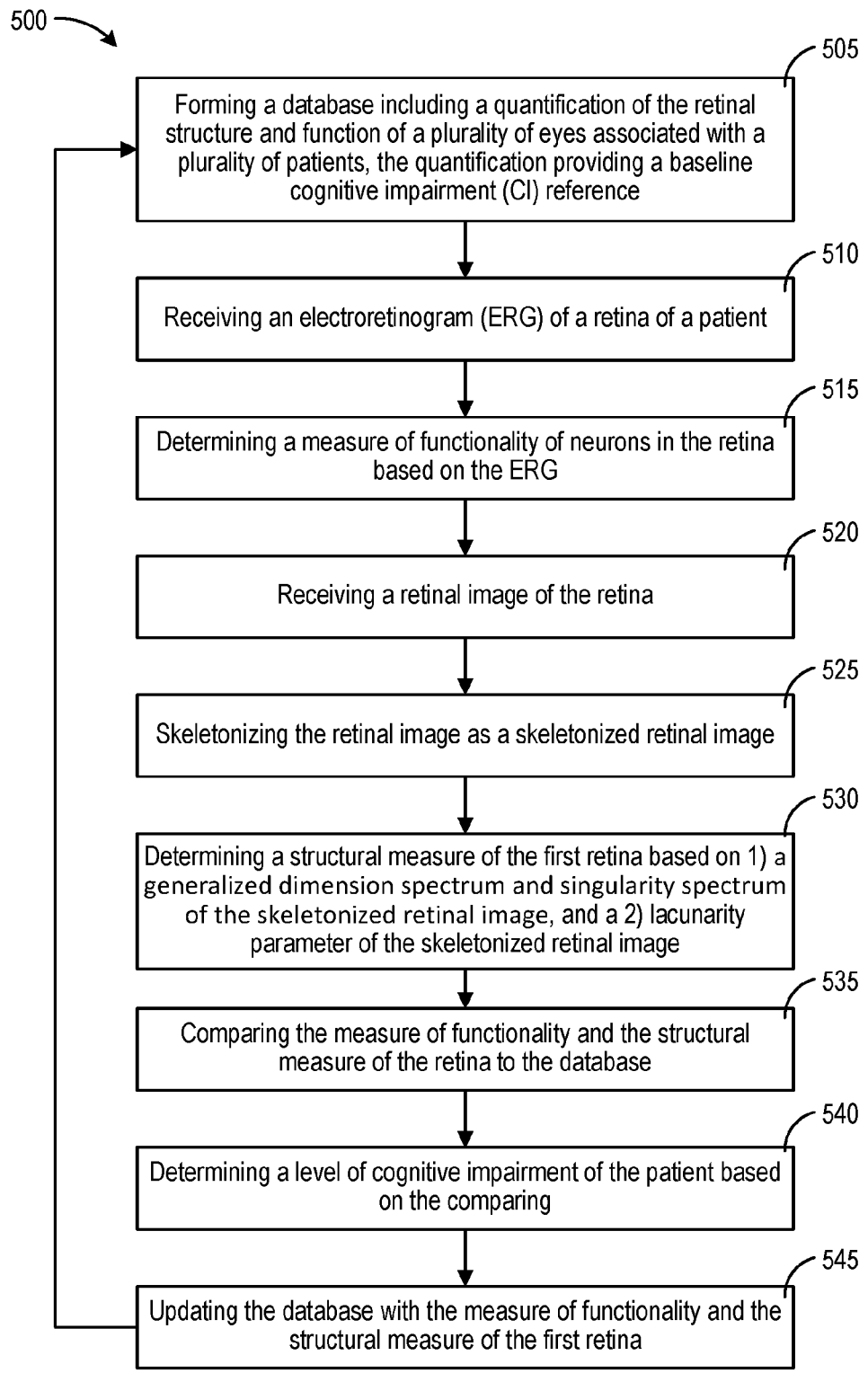
FIG. 5 is a flowchart of an embodiment of a method for diagnosing CI according to the disclosure.

FIG. 5 is a flowchart of an embodiment of a method for diagnosing CI according to the disclosure. A method 500 can begin at block 505. The database 420 can store baseline retinal imagery and data, cognitive assessment data (e.g., of a plurality of patients), and other information.

At block 505 the processor 204 can form a database (e.g., the database 420) including a quantification of the retinal structure and function of a plurality of eyes associated with a plurality of patients that have been subjected to a cognitive assessment. Such a quantification can provide a baseline cognitive impairment (CI) reference paired with the cognitive assessments of the patients. The MoCA, described above is used as a primary example of the cognitive assessment herein, but other cognitive assessment examinations are also applicable.

The baseline data can be based on a plurality of retinal images, ERG data/metrics, fractal dimension, singularity spectrum, and lacunarity calculations for patients in various strata. For example, an initial baseline of patients can be sorted based on MoCA scores associated with respective retinal imagery and structural and functional analysis of the retinal scans and images, as noted above. The baseline data can provide a stratified reference indicating different levels of CI and their associated retinal analysis. In some embodiments, the different strata or levels of CI can be generated using MoCA scores or other cognitive assessments that are aligned or otherwise correlated with structural and functional analyses of retinal images/ERGs. As the retina structural and functional characteristics vary with different levels of CI, the cognitive assessments provide a control for determining the level of CI given the structural and functional analyses.

The database 420 can be updated and thus improved over time as more information (e.g., structural and functional imagery is captured).

At block 520, the processor 404 can receive an electroretinogram (ERG) of a retina of a patient. As noted above, the ERG can provide a functional analysis of the neurons of the patient's retina(s).

At block 515, the processor 404 can determine a measure of functionality of neurons in the retina based on the ERG.

At block 520, the processor 404 can receive a retinal image of the retina. In some implementations, the retinal image can be acquired using a confocal scanning laser ophthalmoscope (e.g., EasyScan™). In some implementations other cameras providing retinal images can also be used. Such imagery can provide a high contrast map of the vascular structure of a retina. In some embodiments, the retinal image can be an optic-disc centered image.

At block 525, the processor 404 can skeletonize the retinal image as a skeletonized retinal image. The skeletonized retinal image can be similar to that shown in FIG. 2. The skeletonized retinal image can allow for analysis of multifractal behavior of the vascular structure of the retina.

In some implementations, the skeletonized retinal image can be divided into smaller subdivisions for individual analysis. In some embodiments, nine subregions can be implemented (see FIG. 3). This is not limiting on the disclosure and other subdivisions (e.g., 6, 10, 12, 16, 20, 25, etc., or any other appropriately divisible number) are possible.

At block 530, the processor 404 can determine a structural measure of the retina based on 1) a generalized dimension spectrum and singularity spectrum of the skeletonized retinal image, and a 2) lacunarity parameter of the skeletonized retinal image. The multifractal behavior in the skeletonized optic-disc centered images can be analyzed using the generalized dimensions ($D_0$, $D_1$, and $D_2$), a lacunarity parameter ($\Lambda$), and singularity spectrum $f(\alpha)$. The $\Lambda$ can be obtained by measuring the gap dispersion inside each retinal image. The multifractal spectra can be calculated to obtain the $f(\alpha)$ and its curve asymmetry.

At block 535, the processor 404 can compare the measure of functionality from block 515 and the structural measure of the retina from block 530 to the data within the database 420.

At block 540, the processor 404 can determine a level of cognitive impairment of the patient based on the comparing. In general, the database 420 can include images and calculations associated with retinal imagery that are known as being received from patients with CI. This provides reference data that can be stratified into various levels of CI. The comparison can thus provide a diagnosis as to whether the patient has CI or not.

At block 545, the processor 404 can then updating the database 420 with the measure of functionality and the structural measure of the first retina to further improve the granularity of the database 420. Accordingly, other measures or assessments of CI (e.g., MoCA, MMSE, PET, MRI) may not be needed given the previously established multimodal strata in the database 420. Thus, using the example of the MoCA, the MoCA score is only used to initially build the multimodal approach that allows identification of the multimodal biomarkers or predictors of CI.

OTHER ASPECTS

The accompanying claims and their equivalents are intended to cover such forms or modifications as would fall within the scope of the disclosure. The various components illustrated in the figures may be implemented as, for example, but not limited to, software and/or firmware on a processor or dedicated hardware. Also, the features and attributes of the specific example embodiments disclosed above may be combined in different ways to form additional embodiments, all of which fall within the scope of the disclosure.

The foregoing method descriptions and the process flow diagrams are provided merely as illustrative examples and are not intended to require or imply that the operations of the various embodiments must be performed in the order presented. As will be appreciated by one of skill in the art the order of operations in the foregoing embodiments may be performed in any order. Words such as "thereafter," "then," "next," etc. are not intended to limit the order of the operations; these words are simply used to guide the reader through the description of the methods. Further, any reference to claim elements in the singular, for example, using the articles "a," "an," or "the" is not to be construed as limiting the element to the singular.

The various illustrative logical blocks, modules, and algorithm operations described in connection with the embodiments disclosed herein may be implemented as electronic hardware, computer software, or combinations of both. To clearly illustrate this interchangeability of hardware and software, various illustrative components, blocks, modules, and operations have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present inventive concept.

The hardware used to implement the various illustrative logics, logical blocks, and modules described in connection with the various embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some operations or methods may be performed by circuitry that is specific to a given function.

In one or more exemplary embodiments, the functions described may be implemented in hardware, software, firmware, or any combination thereof. If implemented in software, the functions may be stored as one or more instructions or code on a non-transitory computer-readable storage medium or non-transitory processor-readable storage medium. The operations of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include random access memory (RAM), read-only memory (ROM), electrically erasable programmable read-only memory (EEPROM), FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer program product.

It is understood that the specific order or hierarchy of blocks in the processes/flowcharts disclosed is an illustration of exemplary approaches. Based upon design preferences, it is understood that the specific order or hierarchy of blocks in the processes/flowcharts may be rearranged. Further, some blocks may be combined or omitted. The accompanying method claims present elements of the various blocks in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects.

Thus, the claims are not intended to be limited to the aspects shown herein, but is to be accorded the full scope consistent with the language claims, wherein reference to an element in the singular is not intended to mean "one and only one" unless specifically so stated, but rather "one or more."

The word "exemplary" is used herein to mean "serving as an example, instance, or illustration." Any aspect described herein as "exemplary" is not necessarily to be construed as preferred or advantageous over other aspects. Unless specifically stated otherwise, the term "some" refers to one or more.

Combinations such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C.

Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, where any such combinations may contain one or more member or members of A, B, or C.

Although the present disclosure provides certain example embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

What is claimed is:

1. A method for determining cognitive impairment (CI) implemented by at least one processor, the method comprising:
   forming a database including a quantification of retinal structure and retinal function of a plurality of eyes associated with a plurality of patients, the quantification providing a baseline cognitive impairment (CI) reference;
   receiving an electroretinogram (ERG) of a retina of a patient;
   determining a measure of functionality of neurons in the retina based on the ERG;
   receiving a retinal image of the retina;
   skeletonizing the retinal image as a skeletonized retinal image;
   determining a structural measure of the first retina based on
      a generalized dimension spectrum and singularity spectrum of the skeletonized retinal image, and
      a lacunarity parameter of the skeletonized retinal image;
   comparing the measure of functionality and the structural measure of the retina to the database; and
   determining a level of cognitive impairment of the patient based on the comparing.

2. The method of claim 1, further comprising updating the database with the measure of functionality and the structural measure of the retina.

3. The method of claim 1, further comprising:
   subdividing the skeletonized retinal image into multiple subregions; and
   determining a structural measure of the each subregion of the multiple subregions based on
      a generalized dimension spectrum and singularity spectrum of each subregion, and
      a lacunarity parameter of each subregion.

4. The method of claim 1, wherein the retinal image comprises an image of an entire branching pattern of the retina observable in a 20°-200° field of view.

5. The method of claim 1, wherein the quantification of the retinal function comprises a plurality of ERGs associated with patients known to have a level of CI.

6. The method of claim 1, wherein the quantification of the retinal structure comprises a plurality of generalized dimension spectrum and a singularity spectrum associated with retinal images associated within patients known to have a level of CI.

7. The method of claim 1, wherein the database further includes the caliber, asymmetry factor, tortuosity, and network complexity of the retinal microvasculature (arteries and veins) with respect to functional features (e.g., contrast sensitivity, electrical response through ERGs), concomitant with both fractal-vascular and neural analysis.

8. The method of claim 1, wherein lacunarity (A) comprises a measure of coarseness of the skeletonized retinal image.

9. A system for determining cognitive impairment (CI) comprising:
   a database including a quantification of retinal structure and retinal function of a plurality of eyes associated with a plurality of patients, the quantification providing a baseline cognitive impairment (CI) reference; and
   at least one processor configured to
      receive an electroretinogram (ERG) of a retina of a patient,
      determine a measure of functionality of neurons in the retina based on the ERG,
      receive a retinal image of the retina,
      skeletonize the retinal image as a skeletonized retinal image,
      determine a structural measure of the first retina based on
         a generalized dimension spectrum and singularity spectrum of the skeletonized retinal image, and
         a lacunarity parameter of the skeletonized retinal image,
      compare the measure of functionality and the structural measure of the retina to the database, and
      determine a level of cognitive impairment of the patient based on the comparing.

10. The system of claim 9, wherein the one or more processors are further configured to update the database with the measure of functionality and the structural measure of the retina.

11. The system of claim 9, wherein the one or more processors are further configured to:
   subdivide the skeletonized retinal image into multiple subregions; and
   determine a structural measure of the each subregion of the multiple subregions based on
      a generalized dimension spectrum and singularity spectrum of each subregion, and
      a lacunarity parameter of each subregion.

12. The system of claim 9, wherein the retinal image comprises an image of an entire branching pattern of the retina observable in a 20°-200° field of view.

13. The system of claim 9, wherein the quantification of the retinal function comprises a plurality of ERGs associated with patients known to have a level of CI.

14. The system of claim 9, wherein the quantification of the retinal structure comprises a plurality of generalized dimension spectrum and a singularity spectrum associated with retinal images associated within patients known to have a level of CI.

15. The system of claim 9, wherein the database further includes the caliber, asymmetry factor, tortuosity, and network complexity of the retinal microvasculature (arteries and veins) with respect to functional features (e.g., contrast sensitivity, electrical response through ERGs), concomitant with both fractal- vascular and neural analysis.

16. The system of claim 9, wherein lacunarity (A) comprises a measure of coarseness of the skeletonized retinal image.

17. A non-transitory computer-readable medium storing instructions that when executed by one or more processors, cause the one or more processors to:
   form a database including a quantification of retinal structure and retinal function of a plurality of eyes associated with a plurality of patients, the quantification providing a baseline cognitive impairment (CI) reference;
receive an electroretinogram (ERG) of a retina of a patient;
determine a measure of functionality of neurons in the retina based on the ERG;
receiving a retinal image of the retina;
skeletonize the retinal image as a skeletonized retinal image;
determine a structural measure of the first retina based on
a generalized dimension spectrum and singularity spectrum of the skeletonized retinal image, and
a lacunarity parameter of the skeletonized retinal image;
comparing the measure of functionality and the structural measure of the retina to the database; and
determine a level of cognitive impairment of the patient based on the comparing.

18. The non-transitory computer-readable medium of claim 17, further comprising instructions that cause the one or more processors to update the database with the measure of functionality and the structural measure of the retina.

19. The non-transitory computer-readable medium of claim 17, further comprising instructions that cause the one or more processors to update:
subdivide the skeletonized retinal image into multiple subregions; and
determine a structural measure of the each subregion of the multiple subregions based on
a generalized dimension spectrum and singularity spectrum of each subregion, and
a lacunarity parameter of each subregion.

20. The non-transitory computer-readable medium of claim 17, wherein the retinal image comprises an image of an entire branching pattern of the retina observable in a 20°-200° field of view.

* * * * *